United States Patent
Papathanassiu

(10) Patent No.: US 12,060,310 B2
(45) Date of Patent: Aug. 13, 2024

(54) COMPOSITIONS AND METHODS OF USING ITACONIC ACID DERIVATIVES

(71) Applicant: ERGON PHARMACEUTICALS, LLC, Washington, DC (US)

(72) Inventor: Adonia Papathanassiu, Washington, DC (US)

(73) Assignee: ERGON PHARMACEUTICALS LLC, Washington, DC (US)

(*) Notice: Subject to any disclaimer, the term of this patent is extended or adjusted under 35 U.S.C. 154(b) by 839 days.

(21) Appl. No.: 17/255,150

(22) PCT Filed: Jul. 1, 2019

(86) PCT No.: PCT/US2019/040121
§ 371 (c)(1),
(2) Date: Dec. 22, 2020

(87) PCT Pub. No.: WO2020/006557
PCT Pub. Date: Jan. 2, 2020

(65) Prior Publication Data
US 2021/0261495 A1 Aug. 26, 2021

Related U.S. Application Data

(60) Provisional application No. 62/763,735, filed on Jun. 29, 2018.

(51) Int. Cl.
*C07C 229/42* (2006.01)
*A61P 35/00* (2006.01)
*C07C 57/42* (2006.01)

(52) U.S. Cl.
CPC .............. *C07C 229/42* (2013.01); *A61P 35/00* (2018.01); *C07C 57/42* (2013.01)

(58) Field of Classification Search
CPC .......... A61P 29/00; A61P 35/00; A61P 37/06; C07C 229/42; C07C 229/44; C07C 57/42; C07C 57/60
See application file for complete search history.

(56) References Cited

U.S. PATENT DOCUMENTS

| 5,260,479 A | 11/1993 | Singh |
| 6,620,424 B1 | 9/2003 | Kiso et al. |
| 2015/0086986 A1 | 3/2015 | Hiller et al. |

FOREIGN PATENT DOCUMENTS

WO 2017/142855 8/2017

OTHER PUBLICATIONS

Nakamura, I. et al. Transition-Metal-Catalyzed Reactions in Heterocyclic Synthesis. Chem. Rev. 2004, vol. 104, p. 2127, (Year: 2004).*
Anderson (Chem and Biol 10:787-797, 2003) (Year: 2003).*
Thiel (Nature Biotechnol 2:513-519, 2004), (Year: 2004).*
International Search Report, issued Nov. 6, 2019 in corresponding International Patent Application No. PCT/US19/40121.
PUBCHEM-CID: 3016580 Create Date: Aug. 8, 2005 (Aug. 8, 2005) pp. 1-5. p. 2, structure.

* cited by examiner

*Primary Examiner* — Savitha M Rao
(74) *Attorney, Agent, or Firm* — Wenderoth, Lind, & Ponack, LLP; Mark Hissong

(57) ABSTRACT

The present invention is directed to itaconic acid derivatives, compounds comprising the derivatives and methods of using the derivatives in the treatment of cancer, inflammation, and autoimmune diseases.

4 Claims, 7 Drawing Sheets

*CRC: Complete Regression Rate

COMPOSITIONS AND METHODS OF USING ITACONIC ACID DERIVATIVES

FIELD OF THE INVENTION

The invention relates to compounds, which are derivatives of itaconic acid, and to said compounds for use in therapy, to pharmaceutical compositions comprising said compounds, to methods of increasing activation of the immune system, methods of suppressing activation of the immune system, methods of treating diseases characterized by activation of the immune system, suppression of the immune system, aberrant inflammation, or aberrant fibrosis, diseases characterized by expression of IRG1, and methods for treating viral infections, bacterial infections, ischemia, sepsis, bone disease, and cancer comprising administering to a subject in need thereof an effective amount of said compounds, and to the use of said compounds in the manufacture of medicaments.

BACKGROUND OF THE INVENTION

Itaconic acid is a natural bactericidal compound secreted by activated macrophages and microglial cells during bacterial infections; its synthesis requires expression of the Immune-Responsive Gene 1 (IRG1) protein, which catalyzes the decarboxylation of cis-aconitate to produce itaconic acid in the tricarboxylic acid (TCA) cycle (Michelucci A et al. Immune-responsive gene 1 protein links metabolism to immunity by catalyzing itaconic acid production, Proc Natl Acad Sci USA 2013, 110(19):7820-7825). IRG1 is predominantly expressed under pro-inflammatory conditions and in cancer (Pan, J. et al. Immune responsive gene 1, a novel oncogene, increases the growth and tumorigenicity of glioma, Oncology Reports 2014, 32(5): 1957-1966; McNeal, S. et al, Association of Immunosuppression with DR6 Expression during Development and Progression of Spontaneous Ovarian Cancer in Laying Hen Model, J. Immunol Res 2016, 2016:6729379). In addition to its bactericidal activity, itaconic acid and its esters exhibit anti-inflammatory properties (Bagvant, G. et al. Studies on anti-inflammatory and analgesic activities of itaconic acid systems. Part 1: itaconoc acids and diesters, Indian Journal of Pharmaceutical Sciences 1994, 56(3) 80-5). Inhibition of inflammation by itaconic acid has been associated with its ability to inhibit succinate dehydrogenase (Lampropoulou, V. et al. Itaconate links inhibition of succinate dehydrogenase with macrophage metabolic remodeling and regulation of inflammation, Cell Metabolism 2016, 24: 158-166). In Lampropoulou et al., intravenous (i.v.) infusion of dimethylitaconate limited cardiac ischemia-reperfusion injury in a murine model of the disease. The same study indicated that accumulation of endogenous itaconate in macrophages was required for regulation of inflammation. Itaconic acid derivatives have also been shown to exhibit direct antiviral properties (Sethy V. et al. Design, synthesis, and biological evaluation of itaconic acid derivatives as potential anti-influenza agents, J. Med. Chem. 2019, 62(5): 2390-2403).

The structure of itaconic acid is shown in Formula (1).

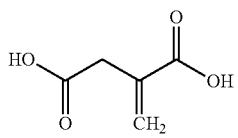

(1)

A diverse number of studies have shown that small organic mono- and di-carboxylic acids, of which of itaconic acid is an example, have unique immunomodulatory properties often through induction of epigenetic changes. Epigenetics is the study of "stably heritable phenotypes resulting from changes in a chromosome without alterations in the DNA sequence" (Berger, S L et al. Genes & Dev. 2009, 23:781-783). For example, monocarboxylic acids such as propionate and butyrate are known histone deacetylases inhibitors (Paul. B. et al. Influences of diet and the gut microbiome on epigenetic modulation in cancer and other diseases, Clin Epigenetics 2015, 7:112). Modulation of histone acetylation by acetate has also been reported (Gao, X. et al. Acetate functions as an epigenetic metabolite to promote lipid synthesis under hypoxia, Nat Comm 2016, 7:11960) and acetate has been shown to optimize memory $CD8^+$ T cell responses (Blamer, M. L. et al. Memory $CD8^+$ T cells require increased concentrations of acetate induced by stress for optimal function, Immunity 2016, 44:1312-1324). The dicarboxylic acid L(S)-2-hydroxyglutarate (S-2HG) is known to reduce histone demethylation (Shim, E. H. et al. L-2-Hydroxyglutarate: an epigenetic modifier and putative on cometabolite in renal cancer, Cancer Discov., 2014, 4(11): 1290-8). S-2HG was also shown to alter global levels of various histone lysine methylation sites in $CD8^+$ T cells, to promote effector differentiation, and to exhibit anti-tumor properties (Tyrakis, P. et al. S-2-hydroxyglutarate regulates $CD8^+$ T-lymphocyte fate, Nature 2016, 540: 236-241).

T cells are typically identified by the presence of CD3, a lineage defining receptor. CD3 is present during all stages of T-cell development and is required for T cell activation. CD3 T cells can differentiate to $CD4^+$ or $CD8^+$ T cells. $CD8^+$ T cell differentiation from a naïve to an effector state is part of the adaptive immune response to bacterial and viral infections and other immunogenic pathological conditions such as cancer (Williams, M. A. and Bevan, J. E. Effector and memory CTL differentiation, Annu. Rev. Immunol. 2007, 25:171-192). Following antigen encounter and T-cell receptor (TCR) engagement, $CD8^+$ T cells undergo a period of rapid expansion during which they acquire cytolytic abilities, also referred to as effector functions. Acquisition of an effector phenotype is characterized by the expression of various cytokines including IFNγ, granzyme B (GZMB) and perform. IFNγ inhibits viral replication and exhibits immunostimulatory and immunomodulatory effects. GZMB and perform work jointly to induce cytolysis: perform forms pores in the plasma membrane of the target cells allowing GZMB, a serine protease, to enter into the cytoplasm and trigger a caspase-dependent apoptosis pathway (Pinkoski, M. J. et al, Granzyme B-mediated apoptosis proceeds predominantly through a Bcl-2-inhibitable mitochondrial pathway, J Biol Chem 2001, 276:12060-12067).

Pathogen clearance results in the rapid contraction of effector $CD8^+$ T cells; the majority of these cells die leaving behind only 5-10% of the original cell number. Surviving cells undergo dedifferentiation and become long-lived memory cells. In the case of chronic infections, $CD8^+$ T cells are known to enter a state of unresponsiveness to further stimulation, referred to as exhaustion (Moskophidis, D. et al. Virus persistence in acutely infected immunocompetent mice by exhaustion of antiviral cytotoxic effector T cells, Nature 1993, 362: 758-761). Exhausted $CD8^+$ T cells are hyporesponsive to stimulation, exhibit a reduced ability to lyse target cells, and are characterized by the increased expression of several inhibitory cell surface receptors including PD-1, LAG3, TIM3, and CTLA-4 (Yi. J. S. et al.

T-cell exhaustion: characteristics, causes and conversion, Immunology 2010, 129(4): 474-481). The exhausted phenotype is common in tumor-infiltrating CD8+ T cells (also known as TILs or tumor-infiltrating lymphocytes) and allows for the survival of tumor cells in the presence of a host immune attack (Wherry, E. J. T cell exhaustion, Nat. Immunol. 2011, 12(6):492-496). Expression of inhibitory cell surface receptors by activated CD8+ T cells is considered critical to terminating immune responses and to preserve self-tolerance. T cell exhaustion serves to limit immune reactivity and is shown to be associated with good prognosis in autoimmune disease (Mckinney, E. F. et al. T cell exhaustion, costimulation and clinical outcome in autoimmunity and infection, Nature 2015, 523(7562):612-616). It is well-understood that the fate of CD8+ T cells (differentiation to effector, memory, or exhausted T cells) is programmed in the very early stages of activation. Histone modifications are considered pivotal in determining the destiny of activated CD8+ T cells (Scott-Browne, J. P. et al. Dynamic changes in chromatin accessibility occur in CD8+ T cells responding to viral infection, Immunity 2016, 45(6): 1327-1340).

Myeloid-derived suppressor cells (MDSCs) are immature myeloid cells present under chronic and acute inflammatory conditions. They are found in instances of cancer, where they play a primarily immunosuppressive role, and are known to contribute to the pathogenesis of infectious diseases and sepsis (Schrijver, I. T. et al. Myeloid-derived suppressor cells in sepsis. Front. Immunol. 2019, 10: 327 and Weber, R. et al. Myeloid-Derived Suppressor Cells Hinder the Anti-Cancer Activity of Immune Checkpoint Inhibitors, Front. Immunol. 2018, 9:1310). There are two main subpopulations of MDSCs: polymorphonuclear (PMN-MDSCs) and monocytic (M-MDSCs), distinguished by the presence of specific biomarkers. In mice, PMN-MDSCs are CD11b+Ly-6G+Ly-6C$^{lo}$, whereas N-MDSCs are CD11b+Ly-6G−Ly-6C$^{hi}$. MDSCs are considered progenitors of osteoclasts and tumor associated macrophages. It has been suggested that monocytic MDSCs hinder the entry of tumor infiltrating lymphocytes (TILs) and limit the effects of immunotherapy (Lesokhin, A. M. et al. Monocytic CCR2+ myeloid derived suppressor cells promote immune escape by limiting activated CD8 T cell infiltration into the tumor microenvironment, Cancer Res. 2012, 72(4): 876-886).

SUMMARY OF THE INVENTION

In a first embodiment, the present invention provides itaconic acid derivatives which include compounds encompassed by Formula (2):

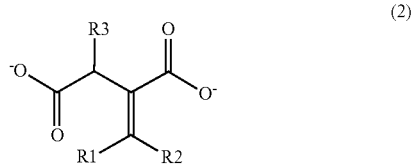

(2)

wherein:
R1, R2, and R3 are independently selected from the group consisting of hydrogen, deuterium, $C_1$-$C_6$ alkyl, $C_2$-$C_6$ alkenyl, $C_2$-$C_6$ alkynyl, $C_3$-$C_{14}$ cycloalkyl, $C_1$-$C_6$ alkylbenzene, aryl, heteroaryl, aryl($C_1$-$C_6$ alkyl), —CN, amino, ($C_1$-$C_6$)alkylamino, dialkyl($C_1$-$C_6$)amino, haloalkyl($C_1$-$C_6$), ($C_1$-$C_6$)alkoxy, ($C_1$-$C_6$)haloalkoxy, heteroaryl($C_1$-$C_6$ alkyl), ($C_4$-$C_{15}$)heterocyclic, ($C_4$-$C_{15}$)heterocyclic($C_1$-$C_6$ alkyl), $C_3$-$C_7$ cycloalkoxy, $C_6$-$C_{10}$-aryloxy, and the moieties (a-1), (a-2), and (a-3), wherein said alkyl, $C_1$-$C_6$ alkylbenzene, aryl, cycloalkyl, heterocyclic, heteroaryl, alkoxy, cycloalkoxy, haloalkyl, or haloalkoxy is further optionally substituted with one or more substituents selected from the group consisting of —$C_1$-$C_6$ alkyl, halo, CN, CF$_3$, —COOH, —OH, —$C_1$-$C_6$ alkoxy, —NH$_2$, —($C_1$-$C_6$ alkyl)NH$_2$, —($C_1$-$C_6$ alkyl)NH($C_1$-$C_6$ alkyl), —($C_1$-$C_6$ alkyl)N($C_1$-$C_6$ alkyl)$_2$, —NH($C_1$-$C_6$ alkyl), —N($C_1$-$C_6$ alkyl)$_2$, —CONH$_2$, —NH(CO)($C_1$-$C_6$ alkyl), —N($C_1$-$C_6$ alkyl)CO($C_1$-$C_6$ alkyl), —SO$_2$—($C_1$-$C_6$ alkyl), —(SO)NH$_2$, (SO)NH($C_1$-$C_6$ alkyl), and (SO)N($C_1$-$C_6$ alkyl)$_2$.

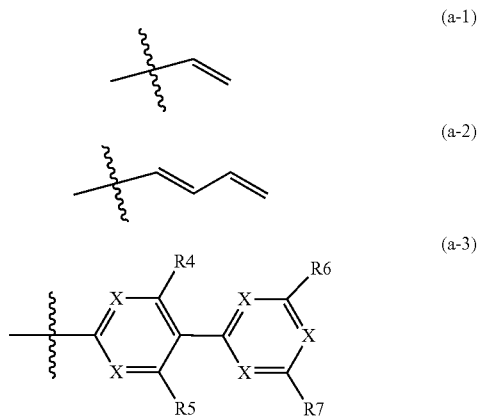

X is either N or CR8, and
R4, R5, R6, R7, and R8 are independently selected from the group consisting of hydrogen, deuterium, $C_1$-$C_6$ alkyl, $C_2$-$C_6$ alkenyl, $C_2$-$C_6$ alkynyl, $C_3$-$C_{14}$ cycloalkyl, $C_1$-$C_6$ alkylbenzene, aryl, heteroaryl, aryl($C_1$-$C_6$ alkyl), —CN, amino, ($C_1$-$C_6$)alkylamino, dialkyl($C_1$-$C_6$) amino, haloalkyl($C_1$-$C_6$), ($C_1$-$C_6$)alkoxy, ($C_1$-$C_6$)haloalkoxy, heteroaryl($C_1$-$C_6$ alkyl), ($C_4$-$C_{15}$)heterocyclic, ($C_4$-$C_{15}$)heterocyclic($C_1$-$C_6$ alkyl), $C_3$-$C_7$ cycloalkoxy, $C_6$-$C_{10}$-aryloxy, wherein said alkyl, $C_1$-$C_6$ alkylbenzene, aryl, cycloalkyl, heterocyclic, heteroaryl, alkoxy, cycloalkoxy, haloalkyl, or haloalkoxy is further optionally substituted with one or more substituents selected from the group consisting of $C_1$-$C_6$ alkyl, halo, CN, CF$_3$, —COOH, —OH, $C_1$-$C_6$ alkoxy, —NH$_2$, —($C_1$-$C_6$ alkyl)NH$_2$, —($C_1$-$C_6$ alkyl)NH($C_1$-$C_6$ alkyl), —($C_1$-$C_6$ alkyl)N($C_1$-$C_6$ alkyl)$_2$, —NH($C_1$-$C_6$ alkyl), —N($C_1$-$C_6$ alkyl)$_2$, —CONH$_2$, —NH(CO)($C_1$-$C_6$ alkyl), —N($C_1$-$C_6$ alkyl)CO($C_1$-$C_6$ alkyl), —SO$_2$—($C_1$-$C_6$ alkyl)-(SO)NH$_2$, (SO)NH($C_1$-$C_6$ alkyl), and (SO)N($C_1$-$C_6$ alkyl)$_2$.

In some embodiments, R1 and R2 are $C_2$-$C_6$ alkyl groups and R3 is hydrogen.

In some embodiments, R1 is H, R2 is an aryl wherein said aryl is further optionally substituted with one or more substituents selected from the group consisting of $C_1$-$C_6$ alkyl, halo, CN, CF$_3$, —COOH, —OH, $C_1$-$C_6$ alkoxy, —NH$_2$, —($C_1$-$C_6$ alkyl)NH$_2$, —($C_1$-$C_6$ alkyl)NH($C_1$-$C_6$ alkyl), —($C_1$-$C_6$ alkyl)N($C_1$-$C_6$ alkyl)$_2$, —NH($C_1$-$C_6$ alkyl), —N($C_1$-$C_6$ alkyl)$_2$, —CONH$_2$, —NH(CO)($C_1$-$C_6$ alkyl), —N($C_1$-$C_6$ alkyl)CO($C_1$-$C_6$ alkyl), —SO$_2$—($C_1$-$C_6$ alkyl)-(SO)NH$_2$, (SO)NH($C_1$-$C_6$ alkyl), and (SO)N($C_1$-$C_6$ alkyl)$_2$ and R3 is —(C$_1$-C$_6$ alkyl)benzene wherein the benzene ring is further optionally substituted with one or more substituents selected from the group consisting of C$_1$-C$_6$ alkyl, halo, CN, CF$_3$, —COOH, —OH, C$_1$-C$_6$ alkoxy, —NH$_2$, —(C$_1$-C$_6$ alkyl)NH$_2$, —(C$_1$-C$_6$ alkyl)NH(C$_1$-C$_6$ alkyl), —(C$_1$-C$_6$ alkyl)N(C$_1$-C$_6$ alkyl)$_2$, —NH(C$_1$-C$_6$ alkyl), —N(C$_1$-C$_6$ alkyl)$_2$, —CONH$_2$, —NH(CO)(C$_1$-C$_6$ alkyl), —N(C$_1$-C$_6$ alkyl)CO(C$_1$-C$_6$ alkyl), —SO$_2$—(C$_1$-C$_6$ alkyl)-(SO)NH$_2$, (SO)NH(C$_1$-C$_6$ alkyl), and (SO)N(C$_1$-C$_6$ alkyl)$_2$.

In some embodiments, R1 is H, R2 is an aryl wherein said aryl is further optionally substituted with one or more substituents selected from the group consisting of C$_1$-C$_6$ alkyl, halo, CN, —COOH, —OH, C$_1$-C$_6$ alkoxy, —NH$_2$, —(C$_1$-C$_6$ alkyl)NH$_2$, —(C$_1$-C$_6$ alkyl)NH(C$_1$-C$_6$ alkyl), —(C$_1$-C$_6$ alkyl)N(C$_1$-C$_6$ alkyl)$_2$, —NH(C$_1$-C$_6$ alkyl), —N(C$_1$-C$_6$ alkyl)$_2$, —CONH$_2$, —NH(CO)(C$_1$-C$_6$ alkyl), and —N(C$_1$-C$_6$ alkyl)CO(C$_1$-C$_6$ alkyl), —(SO)NH$_2$, (SO)NH(C$_1$-C$_6$ alkyl), and (SO)N(C$_1$-C$_6$ alkyl)$_2$, and R3 is group a-1.

The compounds encompassed by Formula (2) expressly exclude itaconic acid of Formula (1) and compounds (3) (IUPAC name: 2-(propan-2-ylidene)butanedioic acid) and (4) (IUPAC name: 2-(phenylmethylidene)butanedioic acid).

The invention also encompasses compounds described by Formula (11):

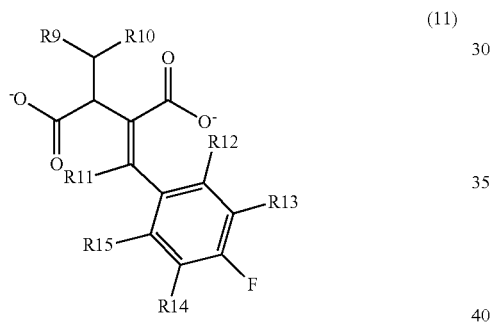

(11)

wherein:
R9, R10, and R11 are independently selected from the group consisting of hydrogen, deuterium, C$_1$-C$_6$ alkyl, C$_2$-C$_6$ alkenyl, C$_2$-C$_6$ alkynyl, C$_3$-C$_{14}$ cycloalkyl, C$_1$-C$_6$ alkylbenzene, aryl, heteroaryl, aryl(C$_1$-C$_6$ alkyl), —CN, amino, (C$_1$-C$_6$)alkylamino, dialkyl(C$_1$-C$_6$) amino, haloalkyl(C$_1$-C$_6$), (C$_1$-C$_6$)alkoxy, (C$_1$-C$_6$)haloalkoxy, heteroaryl(C$_1$-C$_6$ alkyl), (C$_4$-C$_{15}$)heterocyclic, (C$_4$-C$_{15}$)heterocyclic(C$_1$-C$_6$ alkyl), C$_3$-C$_7$ cycloalkoxy, C$_6$-C$_{10}$-aryloxy, and the moieties (a-1), (a-2), and (a-3), wherein said alkyl, C$_1$-C$_6$ alkylbenzene, aryl, cycloalkyl, heterocyclic, heteroaryl, alkoxy, cycloalkoxy, haloalkyl, or haloalkoxy is further optionally substituted with one or more substituents selected from the group consisting of —C$_1$-C$_6$ alkyl, halo, CN, CF$_3$, —COOH, —OH, —C$_1$-C$_6$ alkoxy, —NH$_2$, —(C$_1$-C$_6$ alkyl)NH$_2$, —(C$_1$-C$_6$ alkyl)NH(C$_1$-C$_6$ alkyl), —(C$_1$-C$_6$ alkyl)N(C$_1$-C$_6$ alkyl)$_2$, —NH(C$_1$-C$_6$ alkyl), —N(C$_1$-C$_6$ alkyl)$_2$, —CONH$_2$, —NH(CO)(C$_1$-C$_6$ alkyl), —N(C$_1$-C$_6$ alkyl)CO(C$_1$-C$_6$ alkyl), —SO$_2$—(C$_1$-C$_6$ alkyl), —(SO)NH$_2$, (SO)NH(C$_1$-C$_6$ alkyl), and (SO)N(C$_1$-C$_6$ alkyl)$_2$.

and R12, R13, R14, and R15 are independently selected from the group consisting of hydrogen, deuterium, C$_1$-C$_6$ alkyl, halo, CN, CF$_3$, —COOH, —OH, C$_1$-C$_6$ alkoxy, —NH$_2$, —(C$_1$-C$_6$ alkyl)NH$_2$, —(C$_1$-C$_6$ alkyl)NH(C$_1$-C$_6$ alkyl), —(C$_1$-C$_6$ alkyl)N(C$_1$-C$_6$ alkyl)$_2$, —NH(C$_1$-C$_6$ alkyl), —N(C$_1$-C$_6$ alkyl)$_2$, —CONH$_2$, —NH(CO)(C$_1$-C$_6$ alkyl), —N(C$_1$-C$_6$ alkyl)CO(C$_1$-C$_6$ alkyl), —SO$_2$—(C$_1$-C$_6$ alkyl)-(SO)NH$_2$, (SO)NH(C$_1$-C$_6$ alkyl), and (SO)N(C$_1$-C$_6$ alkyl)$_2$.

In some embodiments, R9, R11, R12, R13, R14, and R15 are hydrogen, and R10 is selected from groups (a-1), (a-2), or (a-3).

The compounds encompassed by Formula (11) expressly exclude Compound (5) (IUPAC name: 2-[(4-fluorophenyl) methylidene]butanedioic acid).

The invention also encompasses compounds described by Formula (12):

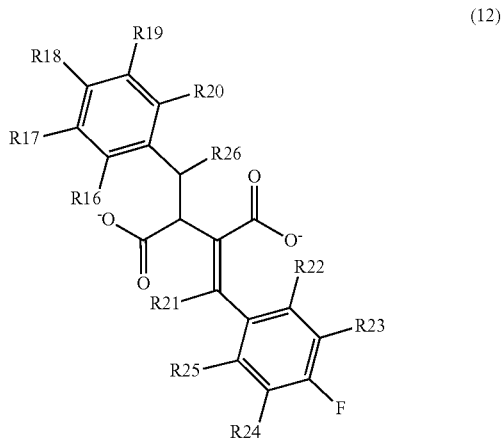

(12)

wherein:
R21 and R26 are independently selected from the group consisting of hydrogen, deuterium, C$_1$-C$_6$ alkyl, C$_2$-C$_6$ alkenyl, C$_2$-C$_6$ alkynyl, C$_3$-C$_{14}$ cycloalkyl, C$_1$-C$_6$ alkylbenzene, aryl, heteroaryl, aryl(C$_1$-C$_6$ alkyl), —CN, amino, (C$_1$-C$_6$)alkylamino, dialkyl(C$_1$-C$_6$)amino, haloalkyl(C$_1$-C$_6$), (C$_1$-C$_6$)alkoxy, (C$_1$-C$_6$)haloalkoxy, heteroaryl(C$_1$-C$_6$ alkyl), (C$_4$-C$_{15}$)heterocyclic, (C$_4$-C$_{15}$)heterocyclic(C$_1$-C$_6$ alkyl), C$_3$-C$_7$ cycloalkoxy, C$_6$-C$_{10}$-aryloxy, and the moieties (a-1), (a-2), and (a-3), wherein said alkyl, C$_1$-C$_6$ alkylbenzene, aryl, cycloalkyl, heterocyclic, heteroaryl, alkoxy, cycloalkoxy, haloalkyl, or haloalkoxy is further optionally substituted with one or more substituents selected from the group consisting of —C$_1$-C$_6$ alkyl, halo, CN, CF$_3$, —COOH, —OH, —C$_1$-C$_6$ alkoxy, —NH$_2$, —(C$_1$-C$_6$ alkyl)NH$_2$, —(C$_1$-C$_6$ alkyl)NH(C$_1$-C$_6$ alkyl), —(C$_1$-C$_6$ alkyl)N(C$_1$-C$_6$ alkyl)$_2$, —NH(C$_1$-C$_6$ alkyl), —N(C$_1$-C$_6$ alkyl)$_2$, —CONH$_2$, —NH(CO)(C$_1$-C$_6$ alkyl), —N(C$_1$-C$_6$ alkyl)CO(C$_1$-C$_6$ alkyl), —SO$_2$—(C$_1$-C$_6$ alkyl), —(SO)NH$_2$, (SO)NH(C$_1$-C$_6$ alkyl), and (SO)N(C$_1$-C$_6$ alkyl)$_2$, and R16, R17, R18, R19, R20, R22, R23, R24, and R25 are independently selected from the group consisting of hydrogen, deuterium, C$_1$-C$_6$ alkyl, halo, CN, CF$_3$, —COOH, —OH, C$_1$-C$_6$ alkoxy, —NH$_2$, —(C$_1$-C$_6$ alkyl)NH$_2$, —(C$_1$-C$_6$ alkyl)NH(C$_1$-C$_6$ alkyl), —(C$_1$-C$_6$ alkyl)N(C$_1$-C$_6$ alkyl)$_2$, —NH(C$_1$-C$_6$ alkyl), —N(C$_1$-C$_6$ alkyl)$_2$, —CONH$_2$, —NH(CO)(C$_1$-C$_6$ alkyl), —N(C$_1$-C$_6$ alkyl)CO(C$_1$-C$_6$ alkyl), —SO$_2$—(C$_1$-C$_6$ alkyl)-(SO)NH$_2$, (SO)NH(C$_1$-C$_6$ alkyl), and (SO)N(C$_1$-C$_6$ alkyl)$_2$.

In some embodiments, R16, R17, R19, R20, R21, R22, R25, and R26 are hydrogen, R23 and R24 are H or —CH$_3$, and R18 is selected from the group consisting of hydrogen, deuterium, C₁-C₆ alkyl, halo, CN, CF₃, —COOH, —OH, C₁-C₆ alkoxy, —NH₂, —(C₁-C₆ alkyl)NH₂, —(C₁-C₆ alkyl)NH(C₁-C₆ alkyl), —(C₁-C₆ alkyl)N(C₁-C₆ alkyl)₂, —NH(C₁-C₆ alkyl), —N(C₁-C₆ alkyl)₂, —CONH₂, —NH(CO)(C₁-C₆ alkyl), —N(C₁-C₆ alkyl)CO(C₁-C₆ alkyl), —SO₂—(C₁-C₆ alkyl)-(SO)NH₂, (SO)NH(C₁-C₆ alkyl), and (SO)N(C₁-C₆ alkyl)₂.

In particular aspects, the itaconic acid derivative of the invention is one of the following compounds:

2-benzyl-3-[(4-flurophenyl)methylidene]butanedioic acid (compound (6)),

2-[(4-flurophenyl)methylidene]-3-(prop-2-ene-1-yl)butanedioic acid (compound (7)), and 2-[(4-aminophenyl)methyl]-3-[(4-fluorophenyl)methylidene]butanedioic acid (compound (8)).

Compound (3)
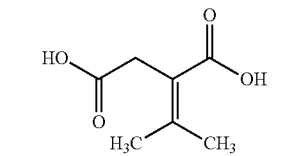

Compound (4)
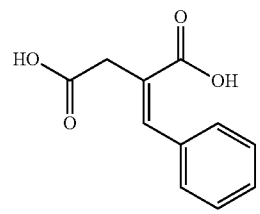

Compound (5)
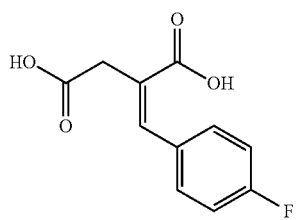

Compound (6)
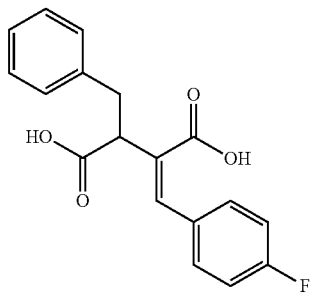

Compound (7)
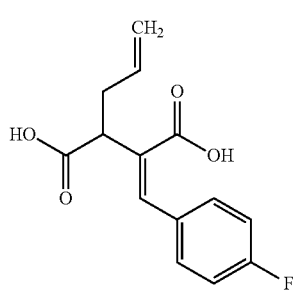

Compound (8)
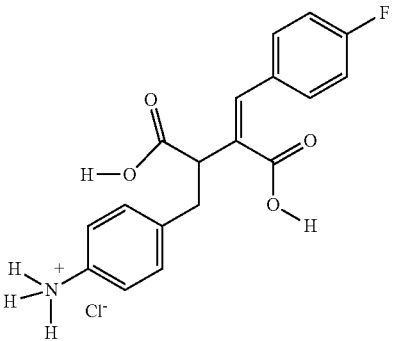

In a second embodiment, the present invention provides methods for treating an inflammatory disorder or disease in a subject (e.g. a mammal such as a human). The method comprises administering to a subject having an inflammatory disorder or disease a therapeutically effective amount of one or more compounds of Formula (2), Formula (11) or Formula (12) or a pharmaceutically acceptable salt of the compound (including all embodiments and combinations of two or more embodiments described herein or any subcombination thereof including pure enantioners and racemic mixtures). In certain aspects, the methods are practiced via administering one or more of Compounds (3), (4), (5), (6), (7), and (8) to the subject. In certain aspects, the disease is characterized by production of pro-inflammatory cytokines including but not limited to one or more of Tumor Necrosis Factor α (TNFα), interleukin (IL)-1B, IL-2, IL-2R, IL-6, IL-7, IL-12, IL-15, IL-17, IL-18, chemokine (C-C motif) ligand 2 (CCL2), C-C-C motif chemokine (CXCL)8, CXCL9, and CXCL10. In further aspects, the production of pro-inflammatory cytokines is related to ischemia and the disease is ischemia. In other aspects, the production of pro-inflammatory cytokines is related to a sepsis syndrome and the disease is sepsis. In other aspects, the production of pro-inflammatory cytokines is related to chronic obstructive pulmonary disease (COPD) and the disease is COPD.

In a third embodiment, the present invention provides methods for treating a disease characterized by the activation of the immune system in a subject (e.g. a mammal such as a human). The method comprises administering to a subject having activation of the immune system a therapeutically effective amount of one or more compounds of Formula (2), Formula (11), or Formula (12) or a pharmaceutically acceptable salt of the compound (including all embodiments and combinations of two or more embodiments described herein or any subcombination thereof including pure enantiomers and racemic mixtures). In certain aspects, the methods are practiced via administering Compound (6), (7) or (8), or a combination of Compounds (6), (7), and (8) to the subject. In certain aspects of this embodiment, the activation of the immune system is aberrant activation of the immune system. In certain aspects, aberrant activation of the immune system is driven by undesired T cell activation. In certain aspects, undesired T cell activation is related to an autoimmune disease or acute allograft rejection.

In a fourth embodiment, the present invention provides methods for treating a subject (e.g. a mammal such as a human) having a disease characterized by aberrant T cell activation. The method comprises administering to a subject having activation of the immune system a therapeutically effective amount of one or more compounds of Formula (2), Formula (11), or Formula (12) or a pharmaceutically acceptable salt of the compound (including all embodiments and combinations of two or more embodiments described herein or any subcombination thereof including pure enantiomers and racemic mixtures). In certain aspects, the methods are practiced via administering Compound (6), (7) or (8), or a combination of Compounds (6), (7), and (8) to the subject. In certain aspects, aberrant T cell activation is related to an autoimmune disease or allograft rejection, including acute allograft rejection.

In a fifth embodiment, the present invention provides methods for treating a subject (e.g. a mammal such as a human) in need of activation of the immune system. The method comprises administering to a subject in need of activation of the immune system a therapeutically effective amount of one or more compounds of Formula (2), Formula (11), or Formula (12) or a pharmaceutically acceptable salt of the compound (including all embodiments and combinations of two or more embodiments described herein or any subcombination thereof including pure enantiomers and racemic mixtures). In certain aspects, the methods are practiced via administering one or more of Compound (6), (7), and (8) to the subject. In certain aspects of this embodiment, the subject has a disease characterized by suppression of the immune system. In certain aspects, the disease is an infectious disease. In other aspects, the disease is cancer.

In a sixth embodiment, the present invention provides methods for treating a subject (e.g. a mammal such as a human) having a disease characterized by suppression of the immune system. The method comprises administering to a subject in need of activation of the immune system a therapeutically effective amount of one or more compounds of Formula (2), Formula (11), or Formula (12) or a pharmaceutically acceptable salt of the compound (including all embodiments and combinations of two or more embodiments described herein or any subcombination thereof including pure enantiomers and racemic mixtures). In certain aspects, the methods are practiced via administering one or more of Compound (6), (7), and (8) to the subject. In certain aspects, the disease is an infectious disease. In other aspects, the disease is cancer.

In a seventh embodiment, the present invention provides methods for treating a disease characterized by the expression of IRG1 in a subject (e.g. a mammal such as a human). The method comprises administering to a subject having a disease characterized by the expression of IRG1 a therapeutically effective amount of one or more compounds of Formula (2), Formula (11), or Formula (12) or a pharmaceutically acceptable salt of the compound (including all embodiments and combinations of two or more embodiments described herein or any subcombination thereof including pure enantiomers and racemic mixtures). In certain aspects, the methods are practiced via administering one or more of Compounds (3), (4), (5), (6), (7), and (8) to the subject. In certain aspects of this embodiment, the expression of IRG1 is aberrant expression of IRG1. In certain aspects, the disease is a neurodegenerative and/or neuroinflammatory diseases. In other aspects the disease is an IRG1-expressing cancer.

In each of the relevant embodiments and aspects of the invention, the therapeutically effective amount of one or more compounds of Formula (2), Formula (11), or Formula (12) is administered to the subject in a pharmaceutical composition comprising the one or more compounds of Formula (2), Formula (11), or Formula (12) and a pharmaceutically acceptable diluent or excipient.

BRIEF DESCRIPTION OF THE DRAWINGS

(FIG. 6A) Compound (6) was given twice a week at 0.2 mg/kg i.p. (FIG. 6B) Compound (6) was given orally twice a day at 3 mg/kg.

DETAILED DESCRIPTION OF THE INVENTION

Figure 1:
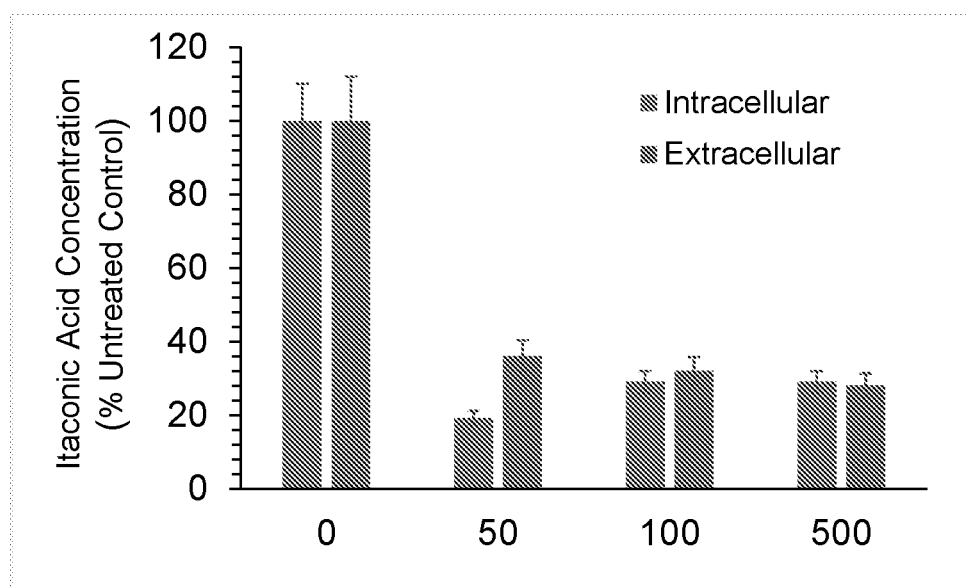
FIG. 1 shows reduced production of itaconic acid from LPS-stimulated human monocyte derived macrophages (hMDMs) after treatment with micromolar concentrations of Compound (6). Left columns(A): intracellular levels of itaconic acid; right columns: extracellular levels of itaconic acid.

Other objects, features and aspects of the present invention are disclosed in, or are obvious from, the following Detailed Description. It is to be understood by one of ordinary skill in the art that the present discussion is a description of exemplary embodiments only and is not intended as limiting the broader aspects of the present invention, which broader aspects are embodied in the exemplary construction.

The present invention comprises itaconate derivatives, e.g., compounds of Formulas (2), (11), or (12) as well as Compounds (3)-(8). These compounds are suitable for the treatment of a human or animal suffering from a disorder characterized by aberrant inflammation such as ischemia, sepsis, and COPD, by the aberrant activation of the adaptive immune system such as an autoimmune disease or allograft rejection, or diseases in need of increased activation of the immune system such as infectious diseases and cancer, and a disease IRG1-expressing diseases such as neurogenerative and neuroinflammatory diseases.

I. DEFINITIONS

As used herein, the term "alkyl" is defined to include saturated aliphatic hydrocarbons including straight chains and branched chains. The term "$C_1$-$C_6$ alkyl," as well as the alkyl moieties of other groups referred to herein (i.e., $C_1$-$C_6$ alkoxy) refers to linear or branched radicals of 1 to 6 carbon atoms (i.e., methyl, ethyl, n-propyl, isopropyl, n-butyl, isobutyl, sec-butyl, terl-butyl, n-pentyl, or n-hexyl). An alkyl group can optionally be substituted by one or more (e.g., 1 to 5) suitable substituents.

As used herein, the term "alkenyl" refers to aliphatic hydrocarbons having at least one carbon-carbon double bond, including straight chains and branched chains having at least one carbon-carbon double bond. The term "$C_2$-$C_6$ alkenyl" means straight or branched chain unsaturated radicals (having at least one carbon-carbon double bond) of 2 to 6 carbon atoms, including, but not limited to, ethenyl, 1-propenyl, 2-propenyl (allyl), isopropenyl, 2-methyl-1-propenyl, 1-butenyl, 2-butenyl, and the like. An alkenyl group optionally can be substituted by one or more (e.g., 1 to 5) suitable substituents. When the compounds of Formula (2) contain an alkenyl group, the alkenyl group may exist as the pure trans-(E) form, the pure cis-(Z) form, or any mixture thereof.

As used herein, the term "alkynyl" refers to aliphatic hydrocarbons having at least one carbon-carbon triple bond, including straight chains and branched chains having at least one carbon-carbon triple bond. The term "$C_2$-$C_6$ alkynyl" refers to straight or branched hydrocarbon chain alkynyl radicals as defined above, having 2 to 6 carbon atoms. An alkynyl group optionally can be substituted by one or more (e.g. 1 to 5) suitable substituents.

As used herein, the term "cycloalkyl" refers to saturated or unsaturated, non-aromatic, monocyclic or polycyclic (such as bicyclic) hydrocarbon rings (e.g., monocyclics such as cyclopropyl, cyclobutyl, cyclopentyl, cyclohexyl, cycloheptyl, cyclooctyl, cyclononyl, or bicyclics including spiro, fused, or bridged systems (such as bicyclo[1.1.1]pentanyl, bicyclo[2.2.1]heptanyl, bicyclo[3.2.1]octanyl or bicyclo[5.2.0]nonanyl, decahydronaphthalenyl, etc.). The cycloalkyl group has 3 to 14 carbon atoms. In some embodiments the cycloalkyl may optionally contain one, two or more non-cumulative non-aromatic double or triple bonds and/or one to three oxo groups. In some embodiments, the bicycloalkyl group has 6 to 14 carbon atoms. For example, the term "$C_3$-$C_{14}$ cycloalkyl" refers to saturated or unsaturated, non-aromatic, monocyclic or polycyclic (such as bicyclic) hydrocarbon rings of 3 to 14 ring-forming carbon atoms (i.e., cyclopropyl, cyclobutyl, cyclopentyl, cyclohexyl, bicyclo[1.1.1]pentanyl, or cyclodecanyl); and the term "$C_3$-$C_7$ cycloalkyl" refers to saturated or unsaturated, non-aromatic, monocyclic or polycyclic (such as bicyclic) hydrocarbon rings of 3 to 7 ring-forming carbon atoms (i.e., cyclopropyl, cyclobutyl, cyclopentyl, cyclohexyl, bicyclo[1.1.1]pentan-1-yl, or bicyclo[1.1.1]pentan-2-yl).

As used herein, the term "aryl" refers to all-carbon monocyclic or fused-ring polycyclic aromatic groups having a conjugated pi-electron system. The aryl group has 6 to 10 carbon atoms in the ring(s). Most commonly, the aryl group has 6 carbon atoms in the ring. For example, as used herein, the term "aryl" means aromatic radicals containing from 6 to 10 carbon atoms such as phenyl or naphthyl. The aryl group can optionally be substituted by 1 or more (e.g., 1 to 5) suitable substituents.

As used herein, the term "alkylbenzene" refers to saturated aliphatic hydrocarbons substituted with a benzene ring having the general formula —$C_nH_{2n+1}(C_6H_5)$, wherein n=1 to 6. The benzene ring can be optionally substituted by 1 or more (e.g., 1 to 5) suitable substituents.

As used herein, the term "heteroaryl" refers to monocyclic or fused-ring polycyclic aromatic heterocyclic groups with one or more heteroatom ring members (ring-forming atoms) each independently selected from O, S and N in at least one ring. The heteroaryl group has 5 to 14 ring-forming atoms, including 1 to 13 carbon atoms, and 1 to 8 heteroatoms selected from O, S and N. In some embodiments, the heteroaryl group has 5 to 10 ring-forming atoms including one to four heteroatoms. The heteroaryl group can also contain one to three oxo or thiono (i.e. =S) groups. In some embodiments, the heteroaryl group has 5 to 8 ring-forming atoms including one, two or three heteroatoms. For example, the term "5-membered heteroaryl" refers to a monocyclic heteroaryl group as defined above with 5 ring-forming atoms in the monocyclic heteroaryl ring; the term "6-membered heteroaryl" refers to a monocyclic heteroaryl group as defined above with 6 ring-forming atoms in the ring; and the term "5- or 6-membered heteroaryl" refers to a monocyclic heteroaryl group as defined above with 5 or 6 ring-forming atoms in the monocyclic heteroaryl ring. For another example, term "5- or 10-membered heteroaryl" refers to a monocyclic or bicyclic heteroaryl group as defined above with 5, 6, 7, 8, 9 or 10 ring-forming atoms in the monocyclic or bicyclic heteroaryl ring. A heteroaryl group optionally can be substituted by 1 or more (e.g., 1 to 5) suitable substituents. Examples of monocyclic heteroaryls include those with 5 ring-forming atoms including one to three heteroatoms or those with 6 ring-forming atoms including one, two or three nitrogen heteroatoms. Examples of fused bicyclic heteroaryls include two fused 5- and/or 6-membered monocyclic rings including one to four heteroatoms. Examples of heteroaryl groups include pyridinyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl (e.g., pyrazol-1-yl, pyrazol-3-yl, pyrazol-4-yl), tetrazolyl, triazolyl (e.g., 1,2,3-triazolyl, 1,2,4-triazolyl), oxadiazolyl (e.g., 1,2,3-oxadiazolyl), thiadiazolyl (i.e., 1,3,4-thiadiazolyl), quinolyl, isoquinolyl, benzothienyl, benzofuryl, indolyl, 1H-imidazo[4,5-c]pyridinyl, imidazo[1,2-a]pyridinyl, 1H-pyrrolo[3,2-c]pyridinyl, imidazo[1,2-a]pyrazinyl, imidazo[2,1-c][1,2,4]triazinyl, imidazo[1,5-a]pyrazinyl, imidazo[1,2-a]pyrimidinyl, 1H-indazolyl, 9H-purinyl, imidazo[1,2-a]pyrimidinyl, [1,2,4]triazolo[1,5-a]pyrimidinyl, [1,2,4]triazolo[4,3-b]pyridazinyl, isoxazolo[5,4-c]pyridazinyl, isoxazolo[3,4-c]pyridazinyl, pyridone, pyrimidone, pyrazinone, pyrimidinone, 1H-imidazol-2(3H)-one, IH-pyrrole-2,5-dione, 3-oxo-2H-pyridazinyl, 1H-2-oxo-pyrimidinyl, 1H-2-oxo-pyridinyl, 2,4(1H,3H)-dioxo-pyrimidinyl, 1H-2-oxo-pyrazinyl, and the like.

As used herein, the term "heterocycloalkyl" refers to a monocyclic or polycyclic (including 2 or more rings that are fused together, including spiro, fused, or bridged systems, for example, a bicyclic ring system), saturated or unsaturated, non-aromatic 4- to 15-membered ring system (such as a 4- to 14-membered ring system, 4- to 12-membered ring system, 5- to 10-membered ring system, 4- to 8-membered ring system, 4- to 6-membered ring system, or 5- to 6-membered ring system), including 1 to 14 ring-forming carbon atoms and 1 to 10 ring-forming heteroatoms each independently selected from O, S and N. The heterocycloalkyl group can also optionally contain one or more oxo or thiono (i.e. =S) groups. For example, the term "4- to 12-membered heterocycloalkyl" refers to a monocyclic or polycyclic, saturated or unsaturated, non-aromatic 4- to 12-membered ring system that comprises one or more ring-forming heteroatoms each independently selected from O, S and N and the term "4- to 10-membered heterocycloalkyl" refers to a monocyclic or polycyclic, saturated or unsaturated, non-aromatic 4- to 10-membered ring system that comprises one or more ring-forming heteroatoms each independently selected from O, S and N. For another example, the term "4- to 6-membered heterocycloalkyl" refers to a monocyclic or polycyclic, saturated or unsaturated, non-aromatic 4- to 6-membered ring system that comprises one or more ring-forming heteroatoms each independently selected from O, S and N, and the term "5- to 6-membered heterocycloalkyl" refers to a monocyclic or polycyclic, saturated or unsaturated, non-aromatic 5- to 6-membered ring system that comprises one or more ring-forming heteroatoms each independently selected from O, S and N. Also included in the definition of heterocycloalkyl are moieties that have one or more aromatic rings (including aryl and heteroaryl) fused to the non-aromatic heterocycloalkyl ring, for example pyridinyl, pyrimidinyl, thiophenyl, pyrazolyl, phthalimidyl, naphthalimidyl, and benzo derivatives of the nonaromatic heterocycloalkyl rings. The heterocycloalkyl group optionally can be substituted by 1 or more (e.g., 1 to 5) suitable substituents. Examples of such heterocycloalkyl rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, quinuclidinyl, chromanyl, isochromanyl, benzoxazinyl, 2-oxaspiro[3.3]heptyl {e.g. 2-oxaspiro[3.3]hept-6-yl}, 7-azabicyclo[2.2.1]heptan-1-yl, 7-azabicyclo[2.2.1]heptan-2-yl, 7-azabicyclo[2.2.1]heptan-7-yl, 2-azabicyclo[2.2.1]heptan-3-on-2-yl, 3-azabicyclo[3.1.0]hexanyl, 3-azabicyclo[4.1.0]heptanyl and the like. Further examples of heterocycloalkyl rings include tetrahydrofuran-2-yl, tetrahydrofuran-3-yl, tetrahydropyranyl (e.g. tetrahydro-2H-pyran-4-yl), imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,3-oxazolidin-3-yl, 1,4-oxazepan-1-yl, isothiazolidinyl, 1,3-thiazolidin-3-yl, 1,2-pyrazolidin-2-yl, 1,2-tetrahydrothiazin-2-yl, 1,3-thiazinan-3-yl, 1,2-tetrahydrodiazin-2-yl, 1,3-tetrahydrodiazin-1-yl, 1,4-oxazin-4-yl, oxazolidinonyl, 2-oxo-piperidinyl (e.g., 2-oxo-piperidin-1-yl), 2-oxoazepan-3-yl, and the like. Some examples of aromatic-fused heterocycloalkyl groups include indolinyl, isoindolinyl, isoindolin-1-one-3-yl, 5,7-dihydro-6H-pyrrolo[3,4-b]pyridin-6-yl, 6,7-dihydro-5H-pyrrolo[3,4-d]pyrimidin-6-yl, 4,5,6,7-tetrahydrothieno[2,3-c]pyridine-5-yl, 5,6-dihydrothieno[2,3-c]pyridin-7(4H)-one-5-yl, 1,4,5,6-tetrahydropyrrolo[3,4-c]pyrazol-5-yl, and 3,4-dihydroisoquinolin-1 (2H)-one-3-yl groups. The heterocycloalkyl group is optionally substituted by 1 or more (e.g., 1 to 5) suitable substituents. Examples of heterocycloalkyl groups include 5- or 6-membered monocyclic rings and 9- or 10-membered fused bicyclic rings.

As used herein, the term "halo" or "halogen" group is defined to include fluorine, chlorine, bromine or iodine.

As used herein, the term "haloalkyl" refers to an alkyl group having one or more halogen substituents (up to perhaloalkyl, i.e., every hydrogen atom of the alkyl group has been replaced by a halogen atom). For example, the term "$C_1$-$C_6$ haloalkyl" refers to $C_1$-$C_6$ alkyl group having one or more halogen substituents (up to perhaloalkyl, i.e., every hydrogen atom of the alkyl group has been replaced by a halogen atom). Examples of haloalkyl groups include $CF_3$, $C_2F_5$, $CHF_2$, $CH_2F$, $CH_2CF_3$ and the like.

As used herein, the term "alkoxy" or "alkyloxy" refers to an —O-alkyl group. For example, the term "$C_1$-$C_6$ alkoxy" or "$C_1$-$C_6$ alkyloxy" refers to an —O—($C_1$-$C_6$ alkyl) group. Examples of alkoxy include methoxy, ethoxy, propoxy (i.e., n-propoxy and isopropoxy), terl-butoxy, and the like. The alkoxy or alkyloxy group optionally can be substituted by 1 or more (e.g., 1 to 5) suitable substituents.

As used here, the term "haloalkoxy" refers to an —O-haloalkyl group. For example, the term "$C_1$-$C_6$ haloalkoxy" refers to an —O—($C_1$-$C_6$ haloalkyl) group. An example of haloalkoxy is —$OCF_3$ or —$OCHF_2$.

As used herein, the term "cycloalkoxy" or "cycloalkyloxy" refers to an —O— cycloalkyl group. For example, the term "$C_3$-$C_7$ cycloalkoxy" or "$C_3$-$C_7$ cycloalkyloxy" refers to an —O—($C_3$-$C_7$ cycloalkyl) group. Examples of cycloalkoxy include cyclopropoxy, cyclobutoxy, cyclopentoxy, cyclohexanoxy, and the like. The cycloalkoxy or cycloalkyloxy group optionally can be substituted by 1 or more (e.g., 1 to 5) suitable substituents.

As used here, the term "$C_6$-$C_{10}$ aryloxy" refers to an —O—($C_6$-$C_{10}$ aryl) group. An example of a $C_6$-$C_{10}$ aryloxy group is —O-phenyl [i.e., phenoxy]. The $C_6$-$C_{10}$ aryloxy group can optionally be substituted by 1 or more (e.g., 1 to 5) suitable substituents.

As used herein, the term "oxo" refers to =O. When an oxo is substituted on a carbon atom, they together form a carbonyl moiety [—C(=O)—]. When an oxo is substituted on a sulfur atom, they together form a sulfinyl moiety [—S(=O)—]; when two oxo groups are substituted on a sulfur atom, they together form a sulfonyl moiety [—S(=O)$_2$-].

As used herein, the term "suitable salts" refers to non-toxic salts formed from the acid of Formulas (2), (11), or (12), including but not limited to Compounds (3)-(8), and a base. Examples of bases include hydroxides of aluminium, zinc, calcium, magnesium, potassium, and sodium, amino acids such as arginine, glycine, and lysine, benzathine, choline, diethylamine, diolamine, meglumine, olamine, and tromethamine.

As used herein, the term "$IC_{50}$" refers to the concentration of a compound needed to reduce a given biological response by 50%.

As used herein, the terms "treat", "treating" and "treatment" have their ordinary and customary meanings, and include one or more of, ameliorating a symptom of a disease, blocking or ameliorating a recurrence of a symptom of a disease, decreasing in severity and/or frequency a symptom of a disease. Treatment means ameliorating, blocking, reducing, decreasing or inhibiting by about 1% to about 100% versus a subject to which the treatment has not been administered. Preferably, the ameliorating, blocking, reducing, decreasing or inhibiting is about 100%, about 99%, about 98%, about 97%, about 96%, about 95%, about 90%, about 80%, about 70%, about 60%, about 50%, about 40%, about 30%, about 20%, about 10%, about 5% or about 1%. The treatment may begin prior to, concurrent with, or after the onset of clinical symptoms of the disease. Thus, the subject may have a disease or merely be susceptible to the disease. The results of the treatment may be permanent or may continue for a period of days (such as 1, 2, 3, 4, 5, 6 or 7 days), weeks (such as 1, 2, 3 or 4 weeks) or months (such as 1, 2, 3, 4, 5, 6 or more months).

The term "subject" is intended to mean an animal, such birds or mammals, including humans and animals of veterinary or agricultural importance, such as dogs, cats, horses, sheep, goats, and cattle.

Cancers for which the compounds of Formulas (2), (11), or (12), including but not limited to Compounds (3)-(8), and pharmaceutically acceptable salts of the foregoing of the invention may be useful in treating include acute lymphoblastic leukemia, acute myeloid leukemia, adrenocortical carcinoma, adrenal cortex cancer, anal, atypical teratoid/phabdoid tumor, basal cell carcinoma, bile duct cancer, bladder cancer, bone cancer (including Ewing sarcoma and osteosarcoma, malignant fibrous histiocytoma), brain tumors (glioblastoma, astrocytoma, neuroblastoma), breast cancer, bronchial cancer, Burkitt lymphoma, gastrointestinal cancer, cardiac cancer, cancer of the central nervous system, cervical cancer, cholangiocarcinoma, chordoma, chronic lymphocytic leukemia, chronic myelogenous leukemia, chronic myeloproliferative neoplasms, colorectal cancer, craniopharyngioma, cutaneous T-cell lymphoma, ductal carcinoma in situ, endometrial cancer, esophageal cancer, extracranial germ tumor, extragonadal germ cell cancer, eye (intraocular, retinoblastoma) cancer, cancer of the fallopian tubes, cancer of the gallbladder, gastric (stomach) cancer, hairy cell leukemia, head and neck cancer, hepatocellular cancer, histiocytosis, Hodgkin Lymphoma, pancreatic cancer, Kaposi's sarcoma, kidney cancer, head and neck cancer, lung cancer, macrooglobulinemia, skin cancer including melanomas, Merkell cell carcinoma, mesothelioma, multiple endocrine neoplasia syndromes, myelodysplastic syndromes, chronic myelogenous leukemia, acute myeloid leukemia, non-Hodgkin lymphoma, ovarian, pancreatic cancer, penile, pharyngeal, pituitary, rhabdomyosarcoma, salivary gland, small intestine cancer, soft tissue sarcoma, cutaneous T-cell lymphoma, testicular cancer, throat cancer, oral cavity, thymoma and thymic carcinoma, thyroid cancer, vaginal cancer, vascular tumors, vulvar cancer, and Wilms tumor.

Autoimmune diseases for which the compounds of Formulas (2), (11), or (12), including but not limited to Compounds (3)-(8), and pharmaceutically acceptable salts of the foregoing of the invention may be useful in treating include Type I or juvenile onset diabetes, rheumatoid arthritis, juvenile rheumatoid arthritis, Reiter's syndrome, systemic lupus erythematosus, alopecia areata, Sjogren's syndrome, systemic sclerosis, autoimmune encephalomyelitis, Balo disease, Bickerstaff's encephalitis, anti-NMDA receptor encephalitis, chronic inflammatory demyelinating polyneuropathy, Guillain-Barre syndrome, idiopathic inflammatory demyelinating diseases, Lambert-Eaton myasthenic syndrome, multiple sclerosis, progressive inflammatory neuropathy, Stiff person syndrome, Sydenham chorea, polymyositis and dermatomyositis, bullous pemphigoid, autoimmune angioedema, autoimmune urticarial vasculitis, cicatricial pemphigoid, dermatitis herpetiformis, epidermolysis bullosa acquisita, erythema nodosum, hidradenitis suppurativa, Lichen planus, Lichen sclerosus, Pemphigus vulgaris, Mucha-Habermann disease, systemic scleroderma, acute motor axonal neuropathy, adiposis dolorosa, Addison's disease, Hashimoto's thyroiditis, Graves' disease, membranous glomerulonephritis, Goodpasture's disease, interstitial cystitis, glanulomatosis, autoimmune enteropathy, Coeliac disease, Crohn's disease, ulcerative colitis, primary biliary cirrhosis, chronic aggressive hepatitis, autoimmune hepatitis, autoimmune metaplastic atrophic gastritis, autoimmune hemolytic anemia, Pernicious anemia, autoimmune lymphoproliferative syndrome, autoimmune neutropenia, autoimmune thrombocytopenia, ankylosing spondylitis, Dercum's disease, adult-onset Still's disease, CREST syndrome, Felty syndrome, IgG4-related diseases, mixed connective tissue disease, relapsing polychondritis, retroperitoneal fibrosis, sarcoidosis, Schnitzler syndrome, myasthenia gravis, myositis, polymyositis, inclusion body myositis, sympathetic ophthalmia, autoimmune retinopathy, autoimmune uveitis, Susac's syndrome, Cogan's syndrome, and autoimmune orchitis, autoimmune myocarditis, autoimmune cardiomyopathy, Coxsackie myocarditis, Dressler's syndrome, autoimmune angioedema, psoriasis, autoimmune polyendocrine syndrome Type 1, 2, and 3, autoimmune pancreatitis, autoimmune inner disease, eosinophilic granulomatosis with polyangiitis, giant cell arteritis, vasculitis, anti-neutrophil cytoplasmic antibody-associated vasculitis, antiphopholipid syndrome, antisynthetase syndrome, aplastic anemia, autoimmune inner ear disease, autoimmune oophoritis, autoimmune retinopathy, autoimmune thrombocytopenia purpura, Behcet's disease, Celiac disease, Churg-Strauss syndrome, Cold agglutinin disease, complex regional pain syndrome, discoid lupus, enthesitis, enthesitis-related arthritis, eosinophilic esophagitis, eosinophilic fasciitis, essential mixed cryoglobulinemia, Evans syndrome, fibromyalgia, gestational pemphigoid, Graves ophthalmopathy, Hashimoto's encephalopathy, Henoch-Schonlein purpura, inflammatory bowel disease, intermediate uveitis, IgA vasculitis, Leukocytostatic vasculitis, Ligneous conjunctivitis, linear IgA disease, lupus nephritis, lupus vasculitis, chronic Lyme disease, Meniere's disease, microscopic colitis, microscopic polyangiitis, Mooren's ulcer, Morphea, neuromyelitis optica, neuromyotonia, Opsoclonus myoclonus syndrome, optic neuritis, Ord's thyroiditis, palindromic rheumatism, paraneoplastic cerebellar degeneration, Parry Romberg syndrome, pediatric autoimmune neuropsychiatric disorder associated with *streptococcus, pityriasis* lichenoides et varioliformis *acuta*, POEMS syndrome, polyarteritis nodosa, polymyalgia rheumatica, postpericardiotomy syndrome, primary immunodeficiency, primary sclerosis cholangitis, pure red cell aplasia, pyoderma gangrenosum, Reynaud phenomenon, reactive arthritis, restless leg syndrome, retroperitoneal fibrosis, rheumatic fever, rheumatoid vasculitis, Schnitzler syndrome, subacute bacterial endocarditis, Tolosa-Hunt syndrome, Transverse myelitis, undifferentiated connective tissue disease, diverticulitis, atopy, immune-mediated myelopathies, and Kawasaki's disease.

Instances of organ transplantation, i.e. induction of allograft tolerance, for which the compounds of Formulas (2), (11), or (12), including but not limited to Compounds (3)-(8), and pharmaceutically acceptable salts of the foregoing of the invention may be useful in treating through the induction of immune tolerance include transplantation of heart, heart-valve, lung, kidney, liver, pancreas, intestine, stomach, testis, hand, cornea, skin, face, islets of Langerhans, bone marrow, blood vessels, and, bone.

Instances of neurodegenerative diseases for which the compounds of Formula (2) and pharmaceutically acceptable salts of the foregoing of the invention may be useful in treating include Alzheimer's disease, Parkinson's disease and PD-related disorders, Prion disease, Motor neuron diseases, Lewy body disease, Alpers' disease, Cerebro-oculofacio-skeletal syndrome (COFS), Corticobasal degeneration, Gerstmann-Straussler-Scheinker Disease, Kuru, Leigh's disease, Monomelic Amyotrophy, Multiple System Atrophy, Multiple System Atrophy with Orthostatic Hypotension (Shy-Drager Syndrome), Neurodegeneration with Brain Iron Accumulation, Opsoclonus Myoclonus, Striatonigral Degeneration, Huntington's disease, amyotrophic lateral sclerosis, spinocerebellar ataxia, Friedreich's ataxia, spinal muscular atrophy, Alexander disease, Alpers-Huttenlocher syndrome, Alpha-methylacyl-CoA racemase (AMACR) deficiency, Andermann syndrome, Arts syndrome, Ataxia neuropathy, Ataxia with oculomotor apraxia, Autosomal dominant cerebellar ataxia, deafness, and narcolepsy (ADCADN), Autosomal recessive spastic ataxia of Charlevoix-Saguenay, Beta-propeller protein-associated neurodegeneration (BPAN), CLN1 disease, CLN2 disease, CLN3 disease, CLN4 disease, CLN5 disease, CLN6 disease, CLN 7 disease, CLN8 disease, CLN10 disease, Congenital insensitivity to pain with anhidrosis (CIPA), Familial encephalopathy with neuroserpin inclusion bodies (FENIB), Fatty acid hydroxylase-associated neurodegeneration (FAHN), GM2-gangliosidosis AB variant, Hereditary sensory and autonomic neuropathy type IE (HSAN IE), Hereditary sensory and autonomic neuropathy type II (HSAN2), Hereditary sensory and autonomic neuropathy type V (HSAN5), Infantile neuroaxonal dystrophy, hereditary spastic paraplegias, Infantile-onset spinocerebellar ataxia (IOSCA), Juvenile primary lateral sclerosis, Marinesco-Sjögren syndrome, Mitochondrial membrane protein-associated neurodegeneration (MPAN), Multiple system atrophy, Neuromyelitis optica, Pantothenate kinase-associated neurodegeneration, Polycystic lipomembranous osteodysplasia with sclerosing leukoencephalopathy (PLOSL), Progressive external ophthalmoplegi, Riboflavin transporter deficiency neuronopathy, Sandhoff disease, and Batten disease.

Instances of inflammation and inflammatory disorder for which the compounds of Formulas (2),(11), or (12), including but not limited to Compounds (3)-(8), and pharmaceutically acceptable salts of the foregoing of the invention may be useful in treating include but not limited to pelvic inflammatory disease, gout, asthma, pleurisy, eczema, arthritis, gastritis, splenitis, sinusitis, hepatitis, nephritis, vasculitis, laryngitis, thyroiditis, prostatitis, pharyngitis, atherosclerosis, allergic reactions, seborrheic dermatitis, Wegener's granulomatosis, arachnoiditis, transmissible spongiform encephalopathies, COPD, and sepsis.

Instances of infectious diseases for which the compounds of Formulas (2), (11), or (12), including but not limited to Compounds (3)-(8), and pharmaceutically acceptable salts of the foregoing of the invention may be useful in treating include *Acinetobacter* infections, actinomycosis, African sleeping sickness, acquired immunodeficiency syndrome (AIDS), amebiasis, anaplasmosis, angiostrongyliasis, anisakiasis, anthrax infection, arcanobacterium *haemolyticum* infection, Argentine Teagan fever, ascariasis, aspergillosis, astrovirus infection, babesiosis, *Bacillus cereus* infection, bacterial pneumonia, bacterial vaginosis, Bacteroide infection, balantidiasis, bartonellosis, *baylisascaris* infection, BK virus infection, Black *piedra*, blastocystosis, bastomycosis, Bolivian hemorrhagic fever, brucellosis, bubonic plague, *Burkholderia* infection, Buruli ulcer, Calicivirus infection, Campylobacteriosis, Candidiasis, Capillariasis, Carrion's disease, Cat-scratch disease, Cellulitis, Chagas Disease, Chancroid, Chickenpox, Chikungunya, *Chlamydia, Chlamydophila pneumoniae* infection, Cholera, Chromoblastomycosis, Chytridiomycosis, Clonorchiasis, *Clostridium difficile* colitis, Coccidioidomycosis, Colorado tick fever, acute viral rhinopharyngitis, Creutzfeldt-Jakob disease, Crimean-Congo hemorrhagic fever, Cryptococcosis, Cryptosporidiosis, Cutaneous larva migrans, Cyclosporiasis, Cysticercosis, Cytomegalovirus infection, Dengue fever, Desmodesmus infection, Dientamoebiasis, Diphtheria, Diphyllobothriasis, Dracunculiasis, Ebola hemorrhagic fever, Echinococcosis, Ehrlichiosis, Enterobiasis, *Enterococcus* infection, Enterovirus infection, Epidemic typhus, Erythema infectiosum, Exanthem subitem, Fasciolasis, Fasciolopsiasis, Fatal familial insomnia, Filariasis, *Clostridium perfringens* infection, Free-living amebic infection, Clostridial myonecrosis, Geotrichosis, Gerstmann-Straussler-Scheinker syndrome, Giardiasis, Glanders, Gnathostomiasis, Gonorrhea, Granuloma inguinale, Group A streptococcal infection, Group B streptococcal infection, *Haemophilus influenzae* infection, Hand foot and mouth disease, Hantavirus Pulmonary Syndrome, Heartland virus disease, *Helicobacter pylori* infection, Hemolytic-uremic syndrome, Hemorrhagic fever with renal syndrome, Hepatitis A, Hepatitis B, Hepatitis C, Hepatitis D, Hepatitis E, Herpes simplex, Histoplasmosis, Hookworm infection, Human bocavirus infection, Human *ewingii* ehrliochiosis, Human papillomavirus infection, Human parainfluenza virus infection, Hymenolepiasis, Epstein-Barr virus infectious mononucleosis, Influenza, Isosporiasis, Keratitis, Kingella Kingae infection, Kuru, Lassa fever, Legionellosis, Leishmaniasis, Leprosy, Leptospirosis, Listeriosis, Lyme Disease, Lymphatic filariasis, Lymphatic choriomeningitis, Malaria, Marburg hemorrhagic fever. Measles, Middle East respiratory syndrome, Melioidosis, Meningitis, Meningococcal disease, Metagonimiasis, Microsporidiosis, Molluscum contagiosum, Monkeypox, Mumps, Murine typhus, *mycoplasma* pneumonia, Mycetoma, Myiasis, Neonatal conjunctivitis, Norovirus, Variant Creutzfeldt-Jakob disease, Nocardiosis, Onchocerciasis, Oristhorchiasis, Paracoccidioidomycosis, Paragonimiasis, Pasteureloosis, Pertussis, Plague, Pneumococcal infection, *Pneumocystis* pneumonia, pneumonia, Poliomyelitis, *Prevotella* infection, Primary Amoebic meningoencephalitis, Progressive multifocal leukoencephalopathy, Psittacosis, Q fever, Rabies, Relapsing fever, Perspiratory syncytial virus infection, Rhinosporiodiosis, Rhinovirus infection, Rickettsial infection, Rickettsialpox, Rift Valley fever, Rocky Mountain spotted fever, Rotavirus infection, Rubella, *Salmonellosis*, Severe Acute Respiratory Syndrome, Scabies, Scarlet fever, Schistosomiasis, Shigellosis, Shingles, Smallpox, Sporotrichosis, Staphylococcal infection, Strongyloidiasis, Subacute sclerosing panencephalitits, Syphilis, Taeniasis, Tetanus, Tineazuelean barbae, Tinea capitis, Tinea corposis, Tinea cruris, Tinea manum, Tinea nigra, Tinea oedis, Tinea unguium, Tinea *versicolor*, Toxocariasis, Toxoplasmosis, Trachoma, Trichinosis, Trichomoniasis, Trichuriasis, Tuberculosis, Tularemia, Typhoid fever, Typhus fever, *Ureaplasma urealyticum* infection, Valley fever, Venezuelan equine encephalitis, Venezuelan hemorrhagic fever, *Vibrio vulnificus* infection, *Vibrio parahaemolyticus* enteritis, Viral pneumonia, West Nile fever, White *Piedra, Yersinia pseudotuberculosis* infection, Yersiniosis, Yellow fever, Zygomycosis, and Zika fever.

Instances of ischemia for which the compounds of Formulas (2), (11), or (12), including but not limited to Compounds (3)-(8), and pharmaceutically acceptable salts of the foregoing of the invention may be useful in treating include cardiac ischemia, coronary artery disease or ischemic heart disease, bowel ischemia, brain ischemia, digital ischemia, limb ischemia, and cutaneous ischemia.

Instances of sepsis syndromes for which the compounds of Formulas (2), (11), or (12), including but not limited to Compounds (3)-(8), and pharmaceutically acceptable salts of the foregoing of the invention may be useful in treating include early sepsis characterized by the presence of infection and bacteremia, sepsis characterized by a dysregulated host response to infection and organ dysfunction, septic shock characterized by circulatory, cellular, and metabolic abnormalities, and multiple organ dysfunction syndrome (MODS).

Instances of neurodegeneration for which the compounds of Formulas (2), (11), or (12), including but not limited to Compounds (3)-(8), and pharmaceutically acceptable salts of the foregoing of the invention may be useful in treating include Alzheimer's disease, Parkinson's disease, Huntington's disease, and amyotrophic lateral sclerosis.

Instances of neuroinflammatory diseases include traumatic brain injury, spinal cord injury, acute disseminated encephalomyelitis, acute optic neuritis, transverse myelitis, neuromyelitis optica, acute flaccid myelitis, and leukomyelitis.

Administration. The compounds of the invention may be used in the methods defined herein. Typically, these compounds will be formulated for in vivo methods and use in a pharmaceutical composition comprising the one or more compounds of Formulas (2), (11), or (12), including but not limited to Compounds (3)-(8), and a pharmaceutically acceptable diluent or excipient.

Formulations comprising the itaconic acid derivative, e.g., the compounds of Formulas (2), (11), or (12), including but not limited to Compounds (3)-(8), may be administered to a subject in need thereof via one or more of topical, oral, rectal and parenteral (intravenous, subcutaneous or intramuscular) routes. The formulations may also be incorporated into biodegradable polymers for sustained release implanted at the disease site. The dosage of the formulations depends on the condition treated, the activity of the drug used, the route of administration, and other clinical factors such as severity of the disease and weight of the patient. The formulations are formulated in ways suitable for the specific route of administration.

Formulations suitable for oral administration include capsules, cachets or tablets containing a predetermined amount of the active ingredient, powder or granules, solutions, suspensions, and emulsions. Formulations suitable for topical administration in the mouth include lozenges, pastilles, and mouthwashes. Formulations suitable for topical administration to the skin include ointments, creams, gels, pastes, and transdermal patches. Formulations for rectal administration may be presented as a suppository with a suitable base, while vaginal administrations maybe presented as pessaries, tampons, creams, gels, pastes, foams, and sprays comprising the active ingredient in an appropriate carrier. Formulations suitable for parenteral administration include aqueous and non-aqueous sterile injection solutions presented in unit-dose or multi-dose containers. It should be also understood that, in addition to the ingredients mentioned above, formulations of this invention might include other agents conventional in the art having regard to the type of formulation in question.

In each of the embodiments of the invention directed to methods of treatment, the formulations may comprise one or more compounds of Formulas (2), (11), or (12), including but not limited to Compounds (3)-(8), alone or the formulations may further comprise a pharmaceutically acceptable excipient. Whether administered alone or in combination with an excipient, formulations comprising one or more itaconic acid derivatives are administered to a subject in an amount which is effective for treating the specific disorder or disease. In general, formulations comprising one or more derivatives are administered to a subject in an amount of from about 0.01 mg/kg to about 100 mg/kg body weight. Acceptable ranges also include: from about 0.01 mg/kg to about 100 mg/kg, 0.1 mg/kg to about 100 mg/kg, 0.1 mg/kg to about 10 mg/kg, 0.1 mg/kg to about 9 mg/kg, 0.1 mg/kg to about 8 mg/kg, 0.1 mg/kg to about 5 mg/kg, 0.5 mg/kg to about 10 mg/kg, 1 mg/kg to about 10 mg/kg, 1.5 mg/kg to about 10 mg/kg and 2 mg/kg to about 10 mg/kg. Specific dosages of itaconic acid derivatives in formulations include: 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5 mg/kg, 6 mg/kg, 7 mg/kg, 8 mg/kg, 9 mg/kg, and 10 mg/kg. However, the amount of the derivative in formulations administered to a subject will vary between wide limits, depending upon the location, source, identity, extent and severity of the disorder or disease, the age and condition of the individual to be treated, etc. A physician will ultimately determine appropriate dosages to be used. Administration frequencies of formulations comprising one or more itaconic acid derivative will also vary depending on factors that include the disease or condition being treated and the modes of administration. Each formulation may be independently administered 4, 3, 2 times or once daily, every other day, every third day, every fourth day, every fifth day, every sixth day, once weekly, every eight days, every nine days, every ten days, bi-weekly, monthly and bi-monthly.

In an embodiment of the invention directed to methods of treatment, the formulation is a composition containing cells (T or NK cells) transduced after treatment with a compound of Formulas (2), (11), or (12), including but not limited to Compounds (3)-(8), for use in adoptive cell therapy in a subject in need thereof.

The invention is further understood by the following non-limiting examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

II. EXAMPLES

Inhibition of IRG1. Itaconic acid levels are a measure of IRG1 expression/activity. To determine the activity of IRG, hMDMs were stimulated with 100 ng/ml LPS for 8 hrs in the presence or absence of the therapeutic agent. Gas chromatography-mass spectroscopy (GC-MS) was used to estimate the intracellular and extracellular concentration of the itaconic acid. In a typical assay, $1-5 \times 10^6$ cells were plated onto a 6-well plate and allowed to adhere overnight. The cells were then stimulated with 0.1-1 µg/mL LPS in the presence or absence of the compound of interest for 8 hrs. The cells were then washed and metabolites were extracted using methanol/water and acetonitrile additions. The aqueous phase of the mixture was dried and metabolites present were derivatized prior to the detection by GC-MS.

In Vitro Inflammation Assay. In vitro inflammation was assessed by measuring the concentration of TNFα in the conditioned media of macrophages stimulated with 0.1-1 µg/mL LPS in the presence or absence of the compound of interest after 4-6 hrs.

In Vivo Inflammation Assay. In vivo inflammation was assessed by measuring the concentration of circulating proinflammatory cytokines in animals injected with LPS. Briefly, C57BL/6 were injected intraperitoneally (i.p.) with 1.5 mg/kg LPS and dosed with vehicle or the therapeutic agent. The animals were bled 2-3 hrs post-LPS injection, sera were obtained, and the levels of proinflammatory cytokines such as TNFα, IL-1B, or IL-6 were determined using commercially available ELISA kits.

Anti-viral Assay. Anti-viral activity was tested using a plaque reduction assay. Through intracellular multiplication, virus particles create circular zones of infected regions or plaques. A plaque reduction assay measured the ability of a drug-candidate to inhibit plaque formation.

Anti-microbial Assay. Bactericidal activity was determined using the agar disk-diffusion assay, which involves the inoculation of agar plates with a standardized inoculum of the test microorganism and the application of the bactericidal agent through the placement of filter papers containing such agent on the agar surface. Diffusion of the bactericidal compound from the filter paper to the agar plate resulted in the inhibitory zones of bacterial growth, which were then measured to assess potency.

Tumor Cell Proliferation Assay. This assay was used to assess the anti-tumor properties of a therapeutic agent in vitro. In a typical proliferation assay, cells were cultured to near confluency in the appropriate media. Subsequently, the cells were trypsinized and plated onto 96-well plates at 2,000 or 5,000 cell per well. The cells were cultured for 48 to 96 hours in the presence or absence of the therapeutic agent. Cell proliferation was then determined using spectrophotometry (MTT assay, BrdU assay) or fluorimetry (Cyquant assay).

Differentiation of T Cells. The ability of T cells to differentiate from a naïve to an effector state was assessed by measuring the levels of IFNγ or GZMB synthesis following activation of the cells using a cocktail of anti-CD2/anti-CD3/anti-CD28 antibodies. Expression of IFNγ, GZMB, and other effector cytokines was measured by determining their concentration in the conditioned media 24-72 hrs after initiation of activation or by estimating the % cells expressing these cytokines using fluorescence-activated cell sorting (FACS).

Epigenetic Modifications. The ability of a therapeutic agent to alter acetylation and/or methylation of histones was assessed by Western Immunoblotting. Briefly, immune and other type cells were collected after being exposed to the therapeutic agent or vehicle control for a specific period of time, typically 24-72 hrs. They were then lysed and cell lysates from control and treated cells contained equal amounts of proteins were subjected to SDS-PAGE electrophoresis. The presence of acetylated and methylated histone sites was determined by Western Immunoblotting using appropriate antibodies.

In Vivo Anti-Tumor Effect. The anticancer properties of the therapeutic agent were evaluated in vivo by determining the ability of the agent to suppress tumor growth and/or increase survival of tumor-bearing animals. In a typical experiment, $0.1$-$1 \times 10^6$ tumor cells, suspended in PBS containing 20% Matrigel, were injected subcutaneously in the right flank of each mouse. When the tumors became palpable, the animals were randomized into different groups and treatment began. In vivo tests routinely included a vehicle control group and different doses and/or routes of administration of the therapeutic agent. Tumor growth was assessed using calipers and the following formula:

Tumor Volume=length×width×width×½

The Kaplan-Meier analysis was used to estimate the survival probability of the tumor-bearing animals.

Tumor Immunophenotyping. To determine the effect of a therapeutic agent on a specific immune cell type in vivo, syngeneic tumor models were employed. In a typical experiment, tumors were allowed to grow to a certain size and were then treated for a specific number of days prior to termination. At the end of the experiment, animals were euthanized, tumors were excised and single cell suspensions were immediately obtained through dissociation of tumor tissues with collagenase. Tumor cell suspensions were then subject to FACS analysis in order to determine the presence of various biomarkers.

Example 1

Synthesis of Compound (6). Compound (6) was synthesized according to the schematic below. Reactants (9) and (10) were commercially available materials. $^1$H NMR (400 MHZ, CDCl$_3$): 2.36 (3H, s), 3.20-3.23 (4H, dd), 3.75 (1H, t), 7.14-7.24 (6H, m), 7.48 (1H, s), 7.81 (2H, m).

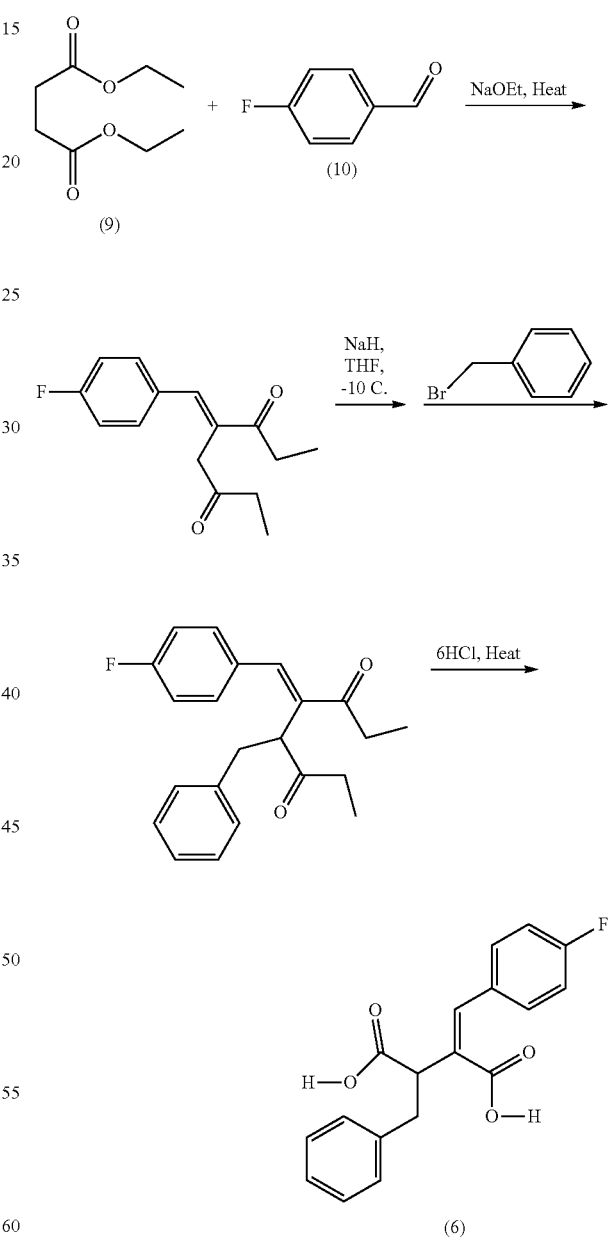

Synthesis of compound (8). Compound (8) was synthesized according to the schematic below. Reactants (9) and (10) are either commercially available or can generally be prepared by conventional techniques known to those skilled in the art.

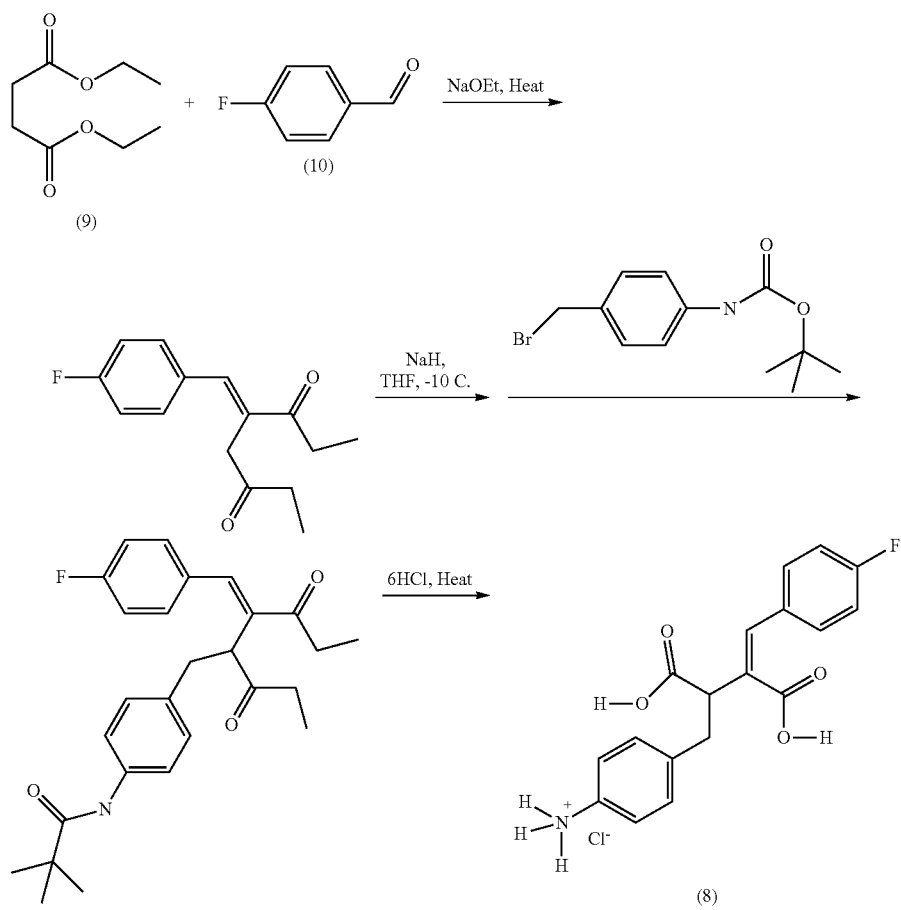

Example 2

Itaconic Acid Synthesis by LPS-Stimulated Macrophages after Treatment with Compound (6). Human monocytes, isolated from peripheral blood and differentiated into macrophages in the presence of 100 ng/ml monocyte colony-stimulating factor (M-CSF) for 5 days, were plated onto a 6-well plate at a density of $1 \times 10^6$ cells/well. The cells were allowed to adhere overnight. They were then pretreated with 0, 50, 100, and 500 μM of Compound (6) for 15 min followed by stimulation with 100 vg/mL LPS for 8 hrs. At the end of the incubation period, cells were washed 2× with PBS. Cells were quenched with 400 μL methanol, previously chilled at −20° C. After addition of ice-cold ultrapure water, cells were collected, vortexed briefly, and allowed to stand on ice for 10 min. Following addition of 400 μL dichloromethane, previously chilled at −20° C., samples were vortexed and centrifuged at 14,000 g at 4° C. for 10 min. The aqueous layer of the samples was collected and dried. Dried materials were dissolved in 20 μL of MOX solution, which was prepared by dissolving 20 mg of methoxamine HCl in 500 μL pyridine for 30 min at room temperature. Metabolites dissolved in MOX were incubated at room temperature for 90 min and subsequently derivatized by adding 80 μL of N-methyl-N-(trimethylsilyl) trifluoroacetamide (MSFTA) at 65° C. for 60 min. Derivatized metabolites were analyzed by GC-MS. The amount of itaconic acid present in the samples was determined after peak integration. The results are shown in FIG. 1. Compound (6) suppressed intracellular and extracellular levels of itaconic acid.

Figure 2:
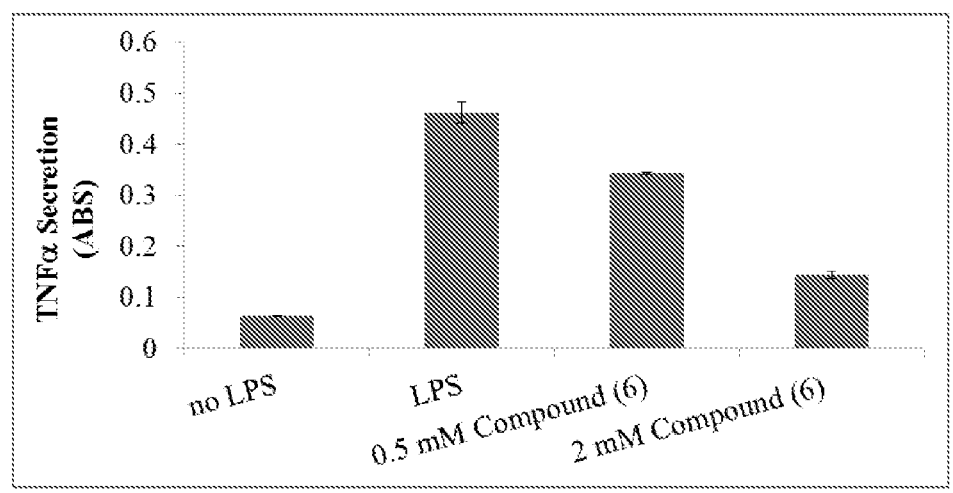
FIG. 2 shows reduced secretion of TNFα from LPS-stimulated human monocyte derived macrophages (hMDMs) after treatment with concentrations of Compound (6) ≥500 μM.

Inhibition of TNFα secretion. hMDMs were pretreated with various concentrations of Compound (6) for 15 min and then stimulated with 1 μg/mL LPS. Conditioned media were collected 6 h later and TNFα concentrations were determined by ELISA. The results, shown in FIG. 2, indicate that the Compound (6) inhibits in vitro inflammation.

Figure 3:
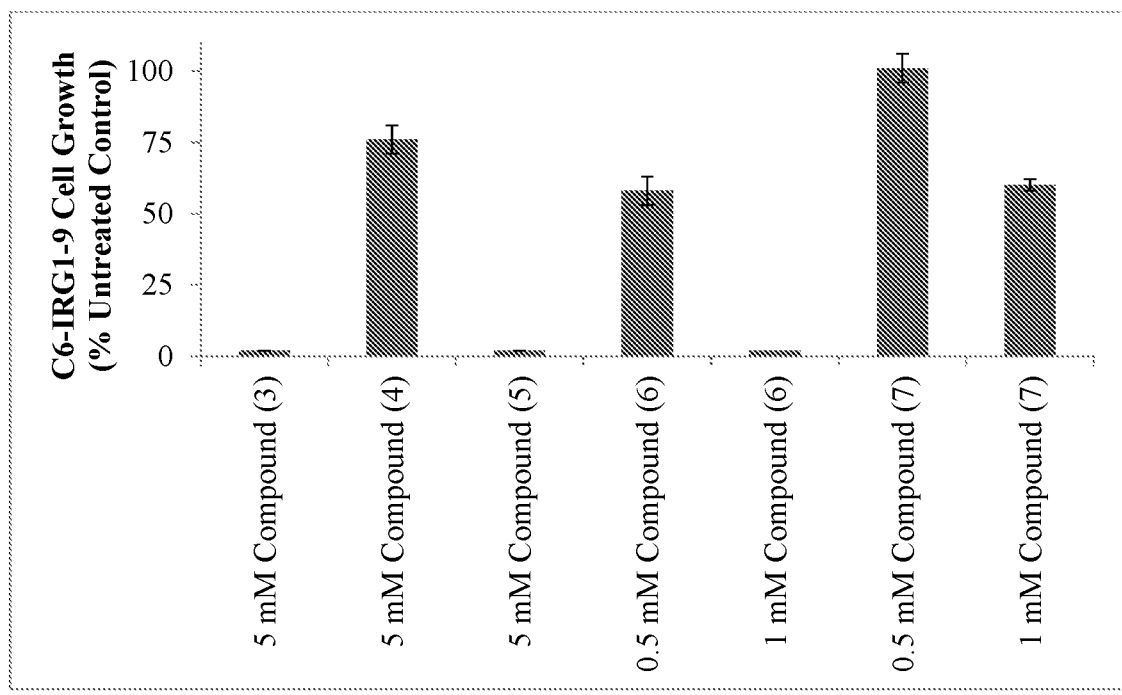
FIG. 3 shows inhibition of proliferation of C6-IRG1-9 rat glioma cells after treatment with various concentrations of compounds (3), (4), (5), (6) and (7).

Inhibition of C6-IRG1-9 Rat Glioma cell proliferation. C6-IRG1-9 cells are rat C6 glioma cells that have been transfected to overexpress IRG1. Overexpression of IRG1 is maintained by culturing the cells in DMEM media containing 0.55 μg/mL puromycin. For the proliferation assays, the cells were plated onto a 96-well plate at a density of 2,000 cells/well. The cells were allowed to adhere overnight; they were subsequently treated with various concentrations of compounds of Formula (2) for 48 hrs. At the end of the incubation period, the number of cells is assessed using the CyQuant Cell Proliferation kit (Thermo Fisher) according to the manufacturer's instructions. The results, shown in FIG. 3, indicate that compounds of Formula (2) are able to reduce or abrogate growth of C6-IRG1-9 cells. In FIG. 3, cell proliferation is expressed as % Untreated Control, defined as:

$$(t-s)*100/(c-s),$$

where t is the number of cells present in a treated well at the end of the incubation period, c is the number of cells present in an untreated well at the end of the incubation period, and s is the initial number of cells in the wells prior to initiation of treatment.

Figure 4:
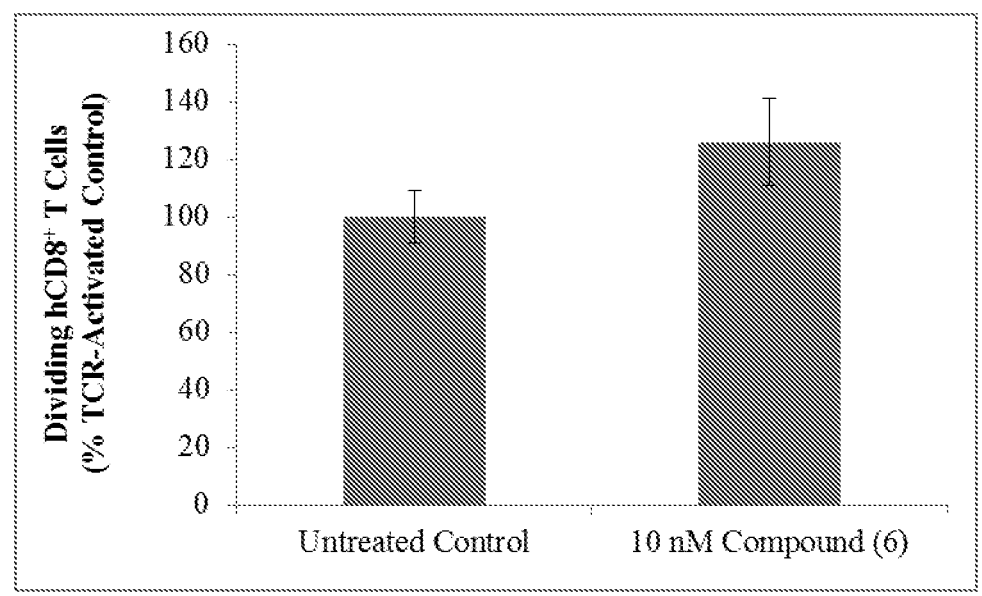
FIG. 4 shows increased proliferation of TCR-activated hCD8$^+$ T cells after treatment with 10 nM of Compound (6).

Augmentation of CD8+ T Cell Proliferation. Naïve hCD8+ T cells were isolated from commercially available buffy coats using magnetic separation and the appropriate kit from Miltenyi Biotec. Cells were then subject to TCR activation using a cocktail of anti-CD2/anti-CD3/anti-CD28 antibodies. Untreated control and treated cells were included in the experiment. The cells were cultured for 72 hrs in TexMACS media (Miltenyi Biotec) without IL-2 and for an additional 48 hrs in TexMACS media containing 20 U human IL-2/mL. Cell division was assessed by flow cytometry using the carboxyfluorescein succimidyl ester (CFSE) dilution method. The results, shown in FIG. 4, indicate that Compound (6) increased proliferation of hCD8+ T cells compared to untreated, TCR-activated control cells.

Augmentation of hCD8+ T Cell Differentiation into Effector T Cells. Naïve CD8+ T cells were isolated from human buffy coats using magnetic separation and the appropriate kit from Miltenyi Biotec. Cells were then activated using a cocktail of anti-CD2/anti-CD3/anti-CD28 antibodies. Differentiation of the cells into effector T cells was assessed by determining the levels of IFNγ and GZMB released into the media at 24 and 72 hrs, respectively using appropriate ELISA kits. Cytokine concentrations were normalized per number of cells present and expressed as % Untreated Control. The results are shown in the Tables 1 and 2 below.

TABLE 1 shows increased synthesis of INFγ following TCR activation of purified human CD8+ (hCD8+) T cells after treatment with low (in the range of 0.1 nM to 100 UM concentrations of Compound (6)) and decrease in IFNγ synthesis with high (>100 μM) concentrations of Compound (6).

TABLE 1

| Compound (6) | IFNγ (% Control) |
| --- | --- |
| 0 (Control) | 100 |
| 1 nM | 129 |
| 10 nM | 510 |
| 100 nM | 274 |
| 10 μM | 370 |
| 100 μM | 198 |
| 500 μM | 47 |

TABLE 2 shows that low concentrations of Compound (6) increase production of GZMB.

TABLE 2

| Compound (6) | Granzyme B (% Control) |
| --- | --- |
| 0 (Control) | 100 |
| 0.1 nM | 117 |
| 1 nM | 165 |

TABLE 2-continued

| Compound (6) | Granzyme B (% Control) |
| --- | --- |
| 10 nM | 504 |
| 100 nM | 276 |
| 10 μM | 360 |

Figure 5:
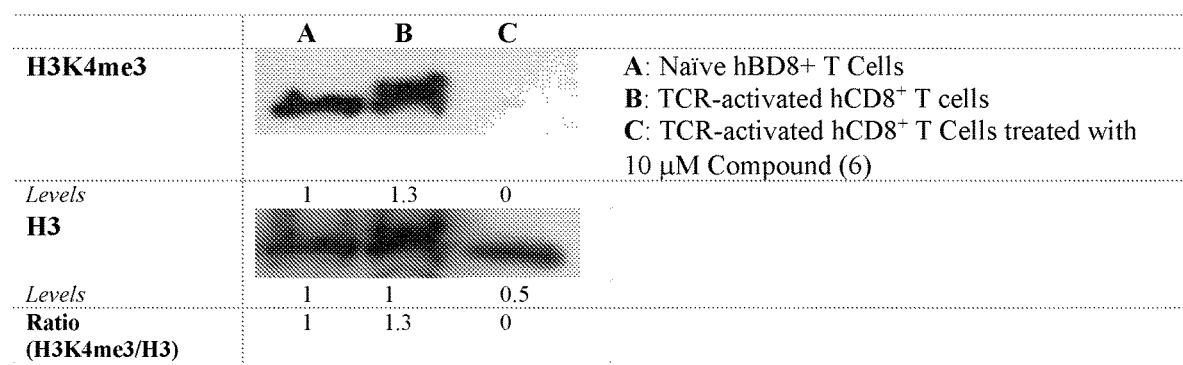
FIG. 5 shows depletion of trimethylation of histone 3 at lysine 4 (H3K4me3) after treatment of TCR-activated hCD8$^+$ T cells with Compound (6). Protein levels were assessed by Western immunoblotting followed by densitometry of the visualized bands. Protein levels of histone 3 (H3) were determined for normalization purposes.

Epigenetic Modification. TCR-activated hCD8+ T cells were exposed to 0 or 10 UM Compound (6) for 72 hrs prior to lysing. Equal amounts of cell lysates were subjected to gel electrophoresis and Western immunoblotting against trimethylated lysine site 4 of histone 3 (H3K4me3). The experiment also included cell lysates from naïve cells. Image J was used for protein quantification. Western immunoblotting against histone 3 (H3) was also performed for normalization purposes. FIG. 5 shows the results of the two Western immunoblotting along with H3K4me3/H3 ratio. Exposure of the hCD8+ T cells to 10 μM Compound (6) led to the depletion of trimethylated H3K4. H3K4me3 is commonly associated with activation of transcription. Depletion of H3K4me3 suggests repression of activation.

Figure 6A:
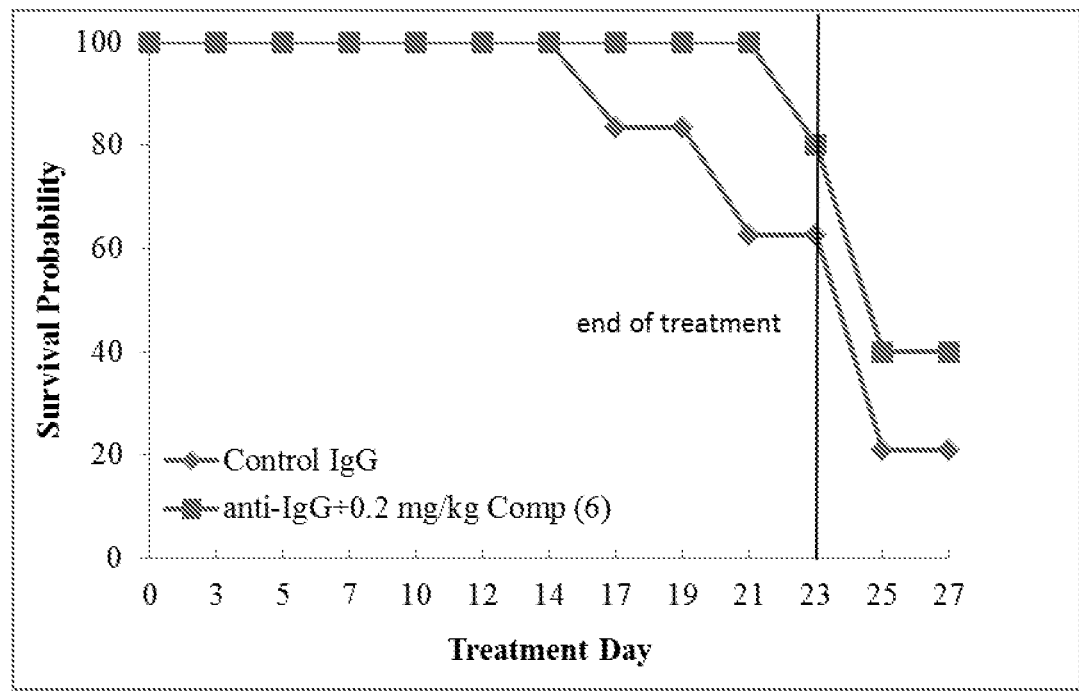
FIGS. 6A & 6B show increased survival of C57BL/6 mice bearing mouse CT26 colorectal tumors after i.p. treatment of the animals with Compound (6).
Figure 6B:
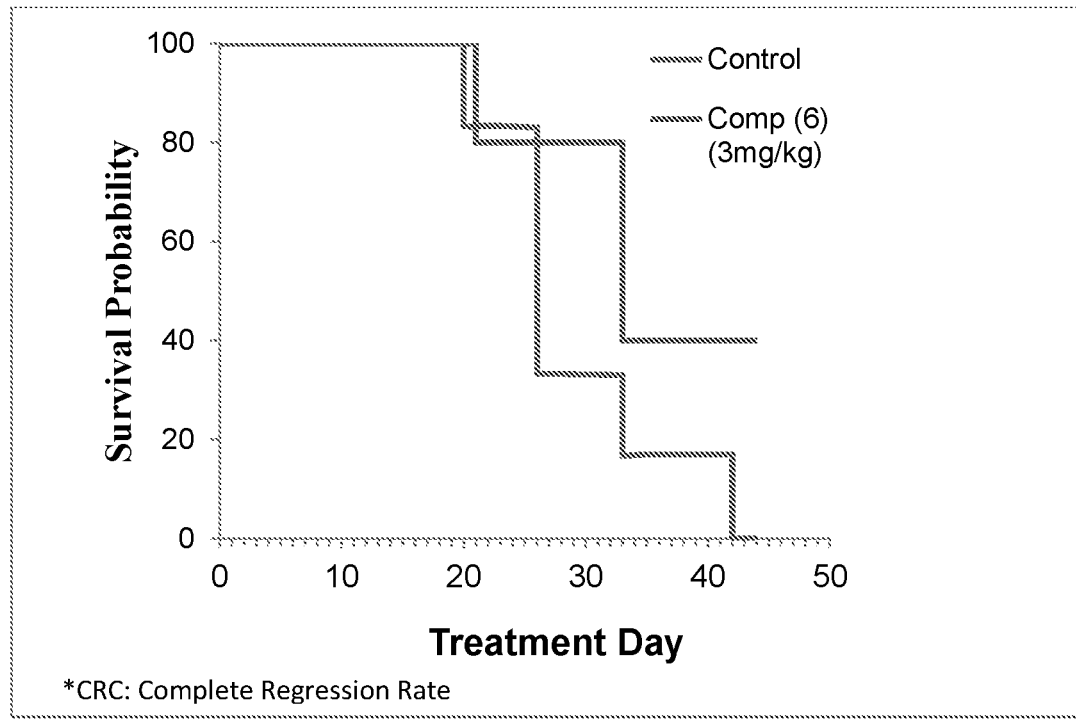

Increased Survival of CT26 Tumor-Bearing Mice. C57BL/6 mice were injected subcutaneously in the right flank with 1×10⁵ CT26 mouse colorectal tumor cells, suspended in PBS containing 20% Matrigel. The tumors were allowed to grow to ~100 mm³. The mice were randomized into two groups (n=6 animals/group): one group received vehicle control and the other group was treated with i.p. injections of 0.2 mg/kg Compound (6) twice a week (Tuesday-Thursday). The experiment continued for 27 days, at which point the mortality rate of control animals was 80%. The Kaplan-Meier survival analysis, shown in FIG. 6A, indicate survival advantage among the animals treated with Compound (6) compared to the animals receiving vehicle control. The experiment was repeated (FIG. 6B). In FIG. 6B, treated animals received oral administrations of 3 mg/kg Compound (6) twice a day. At the end of the experiment, ⅙ animals had experienced complete tumor regression, whereas ⅚ mice exhibited slower tumor growth.

Figure 7:
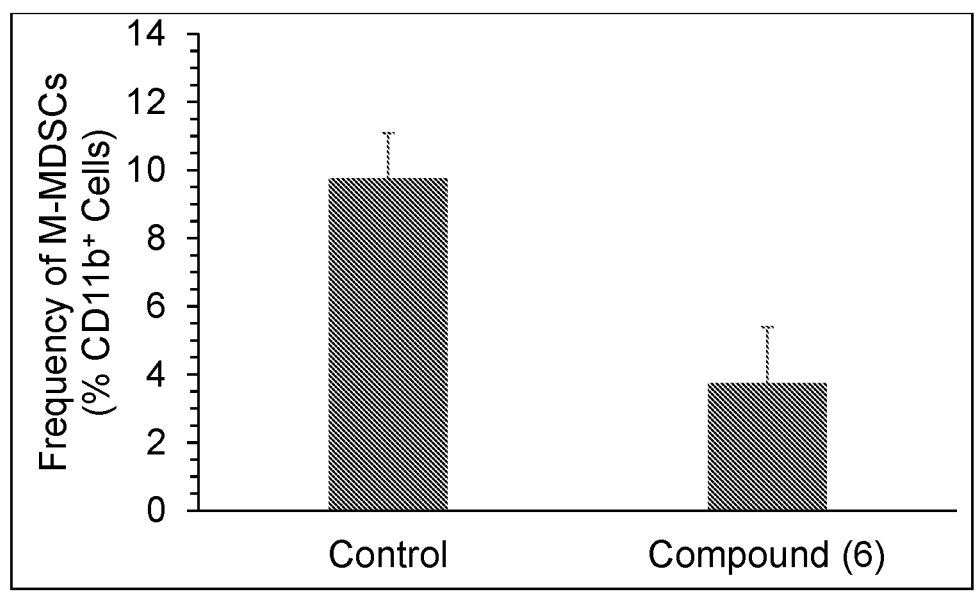
FIG. 7 shows decreased intratumoral frequency of M-MDSCs in tumors treated i.p. with 0.2 mg/kg Compound (6).

Tumor Immunophenotyping of CT26 Tumors. CT26-tumor bearing mice treated with either vehicle control or 0.2 mg/kg Compound (6) (ip, twice a day) were euthanized when the tumors had reached a size of 250-1500 mm³. Tumors were excised and single cell suspensions were obtained using the tumor dissociation kit from Miltenyi Biotec per manufacturer's instructions. The suspensions were analyzed for the presence of MDSCs. FIG. 7 shows that treatment with low concentrations of Compound (6) significantly reduces the intratumoral frequency of M-MDSCs.

What is claimed is:

1. A compound having the following structure:

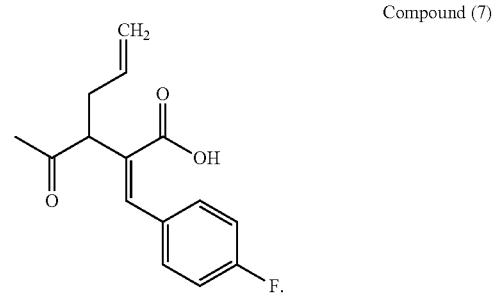 [SMILES: C=CCC(C(C)=O)/C(=C/c1ccc(F)cc1)C(=O)O]

Compound (7)

2. A compound of Formula (12):

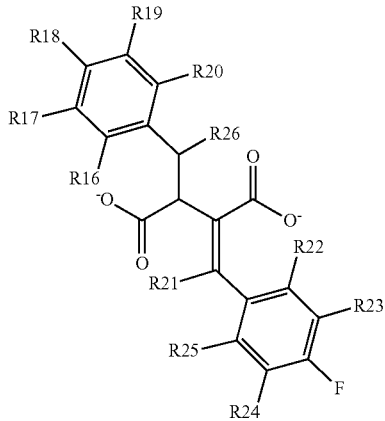

(12)

wherein:
R21 and R26 are hydrogen
R16, R17, R19, R20, R22, and R25 are hydrogen,
R18 is selected from the group consisting of hydrogen, deuterium, $C_1$-$C_6$ alkyl, halo, CN, $CF_3$, —COOH, —OH, $C_1$-$C_6$ alkoxy, —$NH_2$, —($C_1$-$C_6$ alkyl)$NH_2$, —($C_1$-$C_6$ alkyl)NH($C_1$-$C_6$ alkyl), —($C_1$-$C_6$ alkyl)N($C_1$-$C_6$ alkyl)$_2$, —NH($C_1$-$C_6$ alkyl), —N($C_1$-$C_6$ alkyl)$_2$, —$CONH_2$, —NH(CO)($C_1$-$C_6$ alkyl), —N($C_1$-$C_6$ alkyl)CO($C_1$-$C_6$ alkyl), —$SO_2$—($C_1$-$C_6$ alkyl), —(SO)$NH_2$, (SO)NH($C_1$-$C_6$ alkyl), and (SO)N($C_1$-$C_6$ alkyl)$_2$, and
R23 and R24 are hydrogen or —$CH_3$.

3. The compound of claim 2, where R16-R26 are hydrogen, having the structure:

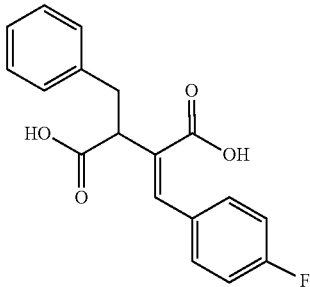

Compound (6)

4. The compound of claim 2, where R16, R17 and R19-R26 are hydrogen and R18 is —$NH_2$, having the structure:

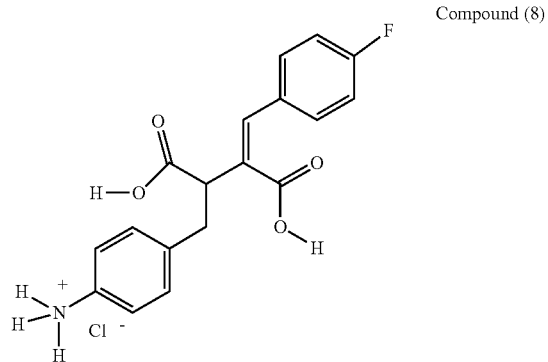

Compound (8)

* * * * *